(12) United States Patent
Biggadike et al.

(10) Patent No.: US 8,754,101 B2
(45) Date of Patent: Jun. 17, 2014

(54) N-CYCLOBUTYL-IMIDAZOPYRIDINE-METHYLAMINE AS TRPV1 ANTAGONISTS

(75) Inventors: Keith Biggadike, Stevenage (GB); Gianpaolo Bravi, Stevenage (GB); Aurelie Cecile Champigny, Stevenage (GB); Diane Mary Coe, Stevenage (GB); Deborah Needham, Stevenage (GB); Daniel Terence Tape, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 14/110,437

(22) PCT Filed: Apr. 5, 2012

(86) PCT No.: PCT/EP2012/056246
§ 371 (c)(1),
(2), (4) Date: Oct. 8, 2013

(87) PCT Pub. No.: WO2012/139963
PCT Pub. Date: Oct. 18, 2012

(65) Prior Publication Data
US 2014/0051720 A1 Feb. 20, 2014

Related U.S. Application Data

(60) Provisional application No. 61/473,868, filed on Apr. 11, 2011.

(51) Int. Cl.
C07D 491/02 (2006.01)
C07D 498/02 (2006.01)
A01N 43/42 (2006.01)
A61K 31/44 (2006.01)

(52) U.S. Cl.
USPC .......................... 514/300; 546/121

(58) Field of Classification Search
USPC .......................... 546/121; 514/300
See application file for complete search history.

(56) References Cited

U.S. PATENT DOCUMENTS

2011/0230467 A1* 9/2011 Shirakami et al. ....... 514/212.08

FOREIGN PATENT DOCUMENTS

| WO | 2005/105798 A1 | 11/2005 |
| WO | 2007/006771 A2 | 6/2007 |
| WO | 2009/095726 A1 | 8/2009 |
| WO | 2010/070452 A1 | 6/2010 |

* cited by examiner

Primary Examiner — Niloofar Rahmani
(74) Attorney, Agent, or Firm — Robert H. Brink

(57) ABSTRACT

A compound of formula (I)

wherein
X represents a H atom, or a $CH_2OH$ group,
Y represents a H atom, or a $CH_2OH$ group,
but X and Y are not both $CH_2OH$ groups
and Ar is selected from or a pharmaceutically acceptable salt thereof.

8 Claims, 3 Drawing Sheets

N-CYCLOBUTYL-IMIDAZOPYRIDINE-METHYLAMINE AS TRPV1 ANTAGONISTS

CROSS-REFERENCE TO RELATED APPLICATIONS

This application is filed pursuant to 35 USC 371 as a United States National Phase Application of International Patent Application Serial No. PCT/EP2012/056246 filed on Apr. 5, 2012, which claims priority from 61/473,868 filed on Apr. 11, 2011 in the United States.

FIELD OF THE INVENTION

The present invention relates to novel compounds, being TRPV1 antagonists having pharmacological activity, to pharmaceutical compositions comprising the compounds and to the use of the compounds in medicine, especially in the treatment of rhinitis, in the treatment of cough or the treatment of asthma.

BACKGROUND OF THE INVENTION

Vanilloids are a class of natural and synthetic compounds that are characterised by the presence of a vanillyl (4-hydroxy 3-methoxybenzyl) group or a functionally equivalent group. A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (*Tetrahedron*, 53, 1997, 4791) and olvanil or —N-(4-hydroxy-3-methoxybenzyl)oleamide (*J. Med. Chem.*, 36, 1993, 2595).

Vanilloid Receptor (VR-1) has now been renamed as TRPV1 (Transient Receptor Potential Vanilloid subfamily member 1). TRPV1 is a calcium-permeable, ligand gated ion channel which is highly expressed in sensory neurones (Caterina M J, Schumacher M A, Tominaga M, Rosen T A, Levine J D and Julius D (1997) Nature 389, 816-824) whose function is modulated by such Vanilloid compounds. TRPV1 has been studied and is extensively reviewed by Szallasi and Blumberg (The American Society for Pharmacology and Experimental Therapeutics, 1999, Vol. 51, No. 2.). TRPV1 plays a key role in peripheral neuronal signalling where it mediates depolarising, excitatory responses to noxious stimuli such as heat, add and capsaicin, the pungent component in chilli peppers (Szallasi et al, Nature Reviews Drug Discovery, 6, 357-372 (2007). TRPV1 acts as a polymodal receptor, responding in an integrative manner to an extensive array of activators including products of inflammation such as histamine, prostaglandins and bradykinin (which activate indirectly via protein kinase A and protein kinase C) as well as eicosanoid derivatives such as HPETEs, anandamide and environmental irritants. Upon activation, the channel pore opens and allows influx of cations which depolarises the nerve membrane and triggers neuronal axonal firing and/or local release of neurotransmitters such as Substance P and CGRP. Activation may be caused by a single trigger, such as pH, but may be caused by integration of different triggers acting in concert on the channel.

The role of TRPV1 in disease has been studied extensively in pain models where a role in both thermal and post-inflammatory hyperalgesia is well established (Chizh et al, Jara-Oseguera et al, 2008). TRPV1 has also been implicated in other diseases where symptoms are potentially driven wholly or in part by neuronal hypersensitivity or hyperactivity, because of its role in sensory signalling in peripheral nerves. Such diseases include asthma, rhinitis, cough, overactive bladder, reflux oesophagitis, irritable bowel syndrome and migraine. TRPV1 has been implicated to have a role in the afferent sensory loop of the cough reflex and the heightened cough sensitivity seen in disease (Grace, Dubuis, Birrell, Belvisi (2012), TRP Channel Antagonists as Potential Antitussives, *Lung* 190: 11-15, and Gu and Lee (2011), Airway irritation and cough evoked by acid: from human to ion channel, *Current Opinion in Pharmacology* 11: 238-247). TRPV1 has been implicated in inflammatory responses occurring in dry eye syndrome (Pan, Wang, Yang, Zhang & Reinach (2010), TRPV1 Activation is Required for Hypertonicity Stimulated Inflammatory Cytokine Release in Human Corneal Epithelial Cells, *Manuscript IOVS,* 10-5801). TRPV1 is also implicated to play a role in metabolic diseases such as diabetes and obesity (Motter A L & Ahern G P (2008) *FEBS Letters* 582, 2257-2262; Suri & Szallasi A (2007), The emerging role of TRPV1 in diabetes and obesity, *Trends in Pharm Sci*, Rasavi et al (2006) *Cell* 127, 1123-1135.)

TRPV1 expression is not limited only to peripheral sensory nerves, but is also expressed in spinal cord and in various regions of the central nervous system. TRPV1 is also found in non-neuronal cells and tissues including various types of epithelial cell and immune cells such as mast cells and dendritic cells (Khairatkar-Joshi N & Szallasi A (2008) *Trends in Molecular Medicine.*

International Patent Applications, Publication Numbers WO 02/08221, WO 02/16317, WO 02/16318 and WO 02/16319 each disclose certain TRPV1 antagonists and their use in the treatment of diseases associated with the activity of TRPV1.

Patent application Number WO 03/022809 discloses urea derivatives including N-(2-Bromophenyl)-N'-[((R)-1-(5-trifluoromethyl-2-pyridyl)pyrrolidin-3-yl)]urea and N-(3-methyl-5-isoquinolinyl))-N'-[(3R)-1-(5-trifluoromethyl-2-pyridyl)pyrrolidin-3-yl)]urea or pharmaceutically acceptable salts thereof and their use in the treatment of diseases associated with the activity of TRPV1.

Patent application Number WO 10/026,129 discloses N-(2-Bromophenyl)-N'-[((R)-1-(5-trifluoromethyl-2-pyridyl)pyrrolidin-3-yl)]urea for use in the treatment of rhinitis. Patent application Number WO 10/026,128 discloses N-(3-methyl-5-isoquinolinyl))-N'-[(3R)-1-(5-trifluoromethyl-2-pyridyl)pyrrolidin-3-yl)]urea for use in the treatment of rhinitis.

It is an object of the invention to provide further TRPV1 antagonists.

BRIEF SUMMARY OF THE INVENTION

In a first aspect of the invention there is provided a compound of formula (I)

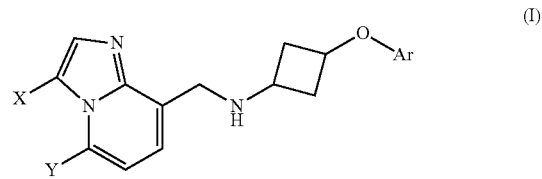

wherein
X represents a H atom, or a CH₂OH group,
Y represents a H atom, or a CH₂OH group,
but X and Y are not both CH₂OH groups
and Ar is selected from

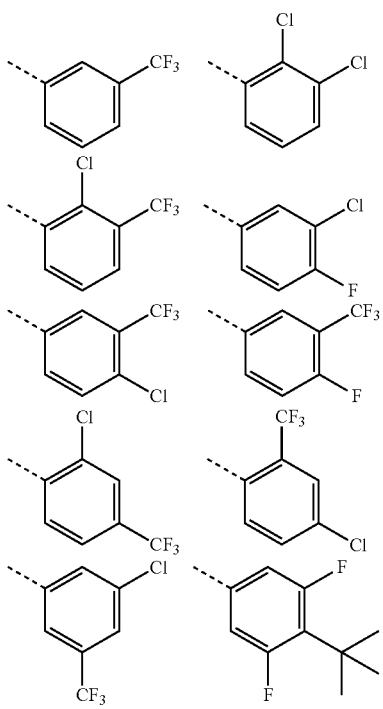

or a pharmaceutically acceptable salt thereof.

Compounds of formula (I) and their pharmaceutically acceptable salts have TRPV1 antagonist activity and are believed to be of potential use for the treatment or prophylaxis of certain disorders, or treatment of the pain associated with them.

Accordingly, in another aspect, the invention provides a compound of formula (I) or a pharmaceutically acceptable salt thereof according to the first aspect for use in therapy.

According to another aspect of the invention there is provided a pharmaceutical composition comprising a compound according to the first aspect, or a pharmaceutically acceptable salt thereof and one or more pharmaceutically acceptable carriers or excipients.

The invention also provides a compound of formula (I) or a pharmaceutically acceptable salt thereof, for use in the treatment of a condition for which a TRPV1 antagonist is indicated, in particular in the treatment and/or prophylaxis of rhinitis, cough or of asthma.

The invention further provides a method for the treatment or prophylaxis of disorders in which antagonism of TRPV1 is beneficial, in a human, which comprises administering a human in need thereof a therapeutically effective amount of a compound of formula (I) or a pharmaceutically acceptable salt thereof.

In particular, the invention provides a method for the treatment of rhinitis which comprises administering to a human in need thereof a therapeutically effective amount of a compound of formula (I) or a pharmaceutically acceptable salt thereof.

The invention also provides a method for the treatment of asthma which comprises administering to a human in need thereof a therapeutically effective amount of a compound of formula (I) or a pharmaceutically acceptable salt thereof.

The invention also provides a method for the treatment of cough which comprises administering to a human in need thereof a therapeutically effective amount of a compound of formula (I) or a pharmaceutically acceptable salt thereof.

The invention provides for the use of a compound of formula (I) or a pharmaceutically acceptable salt thereof in the manufacture of a medicament for the treatment of conditions in which an antagonist of TRPV1 is indicated, particularly rhinitis, cough or asthma.

In another aspect of the invention, there is provided a compound of formula (I) or a pharmaceutically acceptable salt thereof in the manufacture of a medicament for use in the treatment of rhinitis.

Where used herein the term rhinitis is to be understood to include both allergic and non allergic rhinitis. Examples of non-allergic rhinitis include vasomotor rhinitis, irritant rhinitis, occupational rhinitis and NARES (non allergic rhinitis with eosinophils).

In one embodiment the compound of formula (I) or a pharmaceutically acceptable salt thereof is used in the treatment of non allergic rhinitis.

A compound of formula (I) may be prepared by methods described herein.

DETAILED DESCRIPTION OF THE INVENTION

In one aspect of the invention there is provided a compound of formula (I)

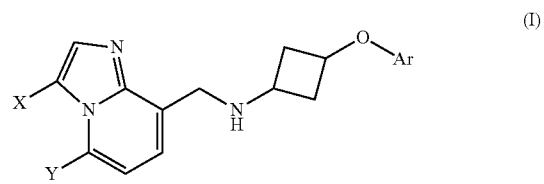

(I)

wherein
X represents a H atom, or a CH₂OH group,
Y represents a H atom, or a CH₂OH group,
but X and Y are not both CH₂OH groups
and Ar is selected from

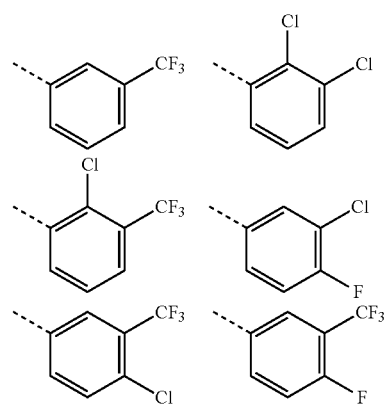

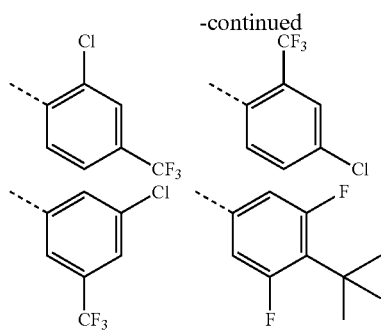

or a pharmaceutically acceptable salt thereof.

It will be appreciated that the present invention covers compounds of formula (I) as the free base and as salts thereof, for example as a pharmaceutically acceptable salt thereof. In one embodiment the compound of formula (I) is in the form of a free base. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid addition salts. For a review on suitable salts see Berge et al., J. Pharm. Sci., 66:1-19, (1977). Suitable pharmaceutically acceptable salts are listed in P H Stahl and C G Wermuth, editors, *Handbook of Pharmaceutical Salts; Properties, Selection and Use*, Weinheim/Surich: Wiley-VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid. Typically, a pharmaceutically acceptable salt may be readily prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain of the compounds described herein can exists as stereoisomers, Accordingly, the present invention encompasses all isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

It will be appreciated from the foregoing that included within the scope of the invention are solvates, isomers and polymorphic forms of the compounds of formula (I) and salts thereof.

In one embodiment, X represents a hydrogen atom, and Y represents a CH$_2$OH group.

In another embodiment, X represents a hydrogen atom and Y represents a hydrogen atom.

In another embodiment X represents a CH$_2$OH group and Y represents a hydrogen atom.

In one embodiment the compound of formula (I) is selected from:

trans-N-(Imidazo[1,2-a]pyridin-8-ylmethyl)-3-{[3-(trifluoromethyl)phenyl]oxy}cyclobutanamine;

trans 3-[(2,3-Dichlorophenyl)oxy]-N-(imidazo[1,2-a]pyridin-8-ylmethyl)cyclobutanamine;

cis-3-[(2,3-dichlorophenyl)oxy]-N-(imidazo[1,2-a]pyridin-8-ylmethyl)cyclobutanamine;

trans-3-{[2-Chloro-3-(trifluoromethyl)phenyl]oxy}-N-(imidazo[1,2-a]pyridin-8-ylmethyl)cyclobutanamine;

trans-3-[(3-Chloro-4-fluorophenyl)oxy]-N-(imidazo[1,2-a]pyridin-8-ylmethyl)cyclobutanamine trifluoroacetates;

trans-3-{[4-Chloro-3-(trifluoromethyl)phenyl]oxy}-N-(imidazo[1,2-a]pyridin-8-ylmethyl)cyclobutanamine;

trans-3-{[4-Fluoro-3-(trifluoromethyl)phenyl]oxy}-N-(imidazo[1,2-a]pyridin-8-ylmethyl)cyclobutanamine;

trans-3-{[2-Chloro-4-(trifluoromethyl)phenyl]oxy}-N-(imidazo[1,2-a]pyridin-8-ylmethyl)cyclobutanamine;

trans-3-{[4-Chloro-2-(trifluoromethyl)phenyl]oxy}-N-(imidazo[1,2-a]pyridin-8-ylmethyl)cyclobutanamine;

trans-3-{[3-Chloro-5-(trifluoromethyl)phenyl]oxy}-N-(imidazo[1,2-a]pyridin-8-ylmethyl)cyclobutanamine;

trans-3-{[4-(1,1-Dimethylethyl)-3,5-difluorophenyl]oxy}-N-(imidazo[1,2-a]pyridin-8-ylmethyl)cyclobutanamine;

cis-3-{[4-(1,1-Dimethylethy)-3,5-difluorophenyl]oxy}-N-(imidazo[1,2-a]pyridin-8-ylmethyl)cyclobutanamine;

{8-[({trans-3-[(2,3-Dichlorophenyl)oxy]cyclobutyl}amino)methyl]imidazo[1,2-a]pyridin-5-yl}methanol;

(8-{[(trans-3-{[4-Fluoro-3-(trifluoromethyl)phenyl]oxy}cyclobutyl)amino]methyl}imidazo[1,2-a]pyridin-5-yl)methanol; or {8-[({trans-3-[(2,3-Dichlorophenyl)oxy]cyclobutyl}amino)methyl]imidazo[1,2-a]pyridin-3-yl}methanol;

cis-3-{[2-Chloro-3-(trifluoromethyl)phenyl]oxy}-N-(imidazo[1,2-a]pyridin-8-ylmethyl)cyclobutanamine; and cis-3-{[4-Fluoro-3-(trifluoromethyl)phenyl]oxy}-N-(imidazo[1,2-a]pyridin-8-ylmethyl)cyclobutanamine or a pharmaceutically acceptable salt thereof.

In one embodiment the compound of formula (I) is trans-3-{[4-Fluoro-3-(trifluoromethyl)phenyl]oxy}-N-(imidazo[1,2-a]pyridin-8-ylmethyl)cyclobutanamine or a pharmaceutically acceptable salt thereof.

Compounds of formula (I) may be in crystalline or non-crystalline form.

COMPOUND PREPARATION

Also disclosed is a process for the preparation of compounds of formula (I) comprising reductive amination of an aldehyde of formula (II)

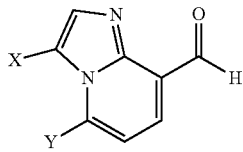
(II)

wherein X and Y are as defined above for compounds of formula (I), with an amine of formula (III),

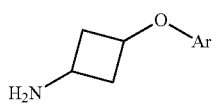
(III)

wherein Ar is as defined above for compounds of formula (I).

This reductive amination may be conducted, for example, using sodium triacetoxyborohydride as reducing agent in a suitable solvent, such as dichloromethane, at a suitable temperature, for example at room temperature. The coupling may also be conducted using alternative, conventional conditions for reductive amination known in the art.

The aldehyde of formula (II) wherein X and Y are both hydrogen is known and is commercially available whereas aldehydes of formula (II) in which either X or Y is a CH$_2$OH group have not been previously described. Compounds of formula (I) in which either X or Y is a CH$_2$OH group may be most conveniently prepared by reductive amination of aldehydes of formula (II) in which this hydroxyl group is suitably protected for example as a MOM (methyoxymethyl) or TBDMS (tert-butyldimethylsilyl)ether followed by deprotection with acid or tetrabutyl ammonium fluoride respectively. Other protecting groups that may be employed for the hydroxyl group and the means for their removal can be found in T. W. Greene 'Protective Groups in Organic Synthesis' 4th Edition, J. Wiley and Sons, 2006, incorporated herein by reference as it relates to such procedures.

Compound of formula (II) in which X is hydrogen and Y is a CH$_2$O-MOM group may be prepared by reduction of the corresponding methyl ester (IV),

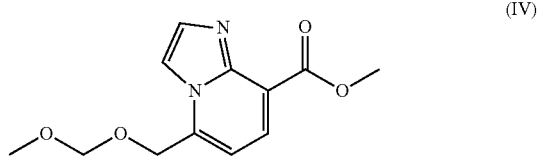
(IV)

This reduction may be conducted for example using sodium bis(2-methoxyethoxy)aluminium hydride (Red-Al) and morpholine in, for example, toluene solution at low temperature, for example −40° C. Other reducing agents known in the art to reduce esters to aldehydes may also be used.

Compound (IV) may be prepared by reaction of the chloro derivative (V),

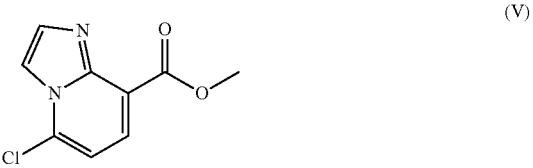
(V)

with tributyl({[(methyloxy)methyl]oxy}methyl)stannane in the presence of chloro(di-2-norbonylphosphino)(2'-dimethylamino-1,1'-biphenyl-2-yl)palladium (II). This reaction may be conducted in a suitable solvent, for example, toluene in a microwave reactor at elevated temperature, for example 170° C., for a period of 1 hour.

The compound of formula (V) may be prepared by reaction of the aminopyridine (VI)

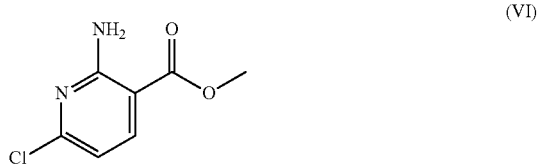
(VI)

with chloroacetaldehyde in the presence of sodium bicarbonate in aqueous methanol at reflux temperature. The compound of formula (VI) is known and is commercially available.

Compound of formula (II) in which Y is hydrogen and X is a CH$_2$O-TBDMS group may be prepared by reduction of the corresponding ethyl ester (VII).

(VII)

This reduction may be conducted, for example, using diisobutylaluminium hydride (DIBAL) in, for example, tetrahydrofuran solution at low temperature, for example −78°

C. Other reducing agents known in the art to reduce esters to aldehydes may also be used.

Compound (VII) may be prepared by protection of the alcohol of formula (VIII),

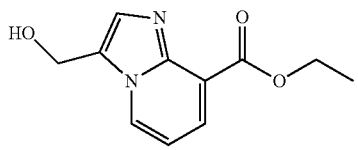

with tert-butyldimethylsilyl chloride in a suitable solvent, for example, dichloromethane, in the presence of a base such as triethylamine and 4-dimethylamino pyridine at 50° C. for 16 hours.

The alcohol of formula (VIII) may be prepared by reaction of the ester of formula (IX),

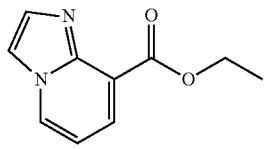

with formaldehyde in the presence of sodium acetate in aqueous acetic acid at reflux temperature for 4 hours. The compound of formula (IX) is known and is commercially available.

Compounds of formula (III) may be prepared by reaction of phenols of formula (X),

Ar—OH      (X)

wherein Ar is as defined above for compounds of formula (I) with an aminocyclobutanol derivative of formula (XI),

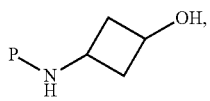

wherein P is a suitable protecting group such as a BOC (tert-butyloxycarbonyl) group, followed by removal of the protecting group. Examples of other protecting groups that may be employed in the synthetic routes described herein and the means for their removal can be found in T. W. Greene 'Protective Groups in Organic Synthesis'; 4th Edition, J. Wiley and Sons, 2006, incorporated herein by reference as it relates to such procedures.

This ether formation may be conducted, for example, using Mitsunobu conditions by reacting the phenol (X) with the protected aminocyclobutanol (XI) in the presence of diisopropylazodicarboxylate and triphenylphosphine in a suitable solvent such as tetrahydrofuran. Variants of the Mitsunobo reaction such as that described by Tsunoda (*Tetrahedron Letters*, 35, 5081, 1994) using cyanomethyenetributylphosphorane (CMBP) in toluene may also be used. The Mitsunobo reaction takes place with inversion of configuration such that if the input aminocyclobutanol (XI) has the trans configuration the product will have a cis configuration, and if the input aminocyclobutanol (XI) has the cis configuration the product will have a trans configuration. Where the protecting group is a BOC group this can then be removed under acidic conditions, for example, using hydrochloric acid in dioxane, or TFA in dichloromethane to give compounds of formula (III).

Phenols of formula (X), wherein Ar is as defined for compounds of formula (I), are known and are commercially available.

Compounds of formula (XI) in which P is a BOC group are known and are commercially available in racemic form and also as individual cis and trans isomers.

A second process for the preparation of compounds of formula (I) where X and Y are both hydrogen comprises reaction of a compound of formula (XII),

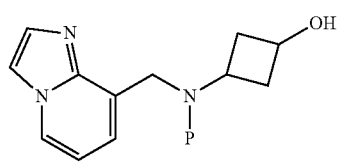

where P is a suitable protecting group such as a BOC group, with a phenol of formula (X), followed by removal of the protecting group.

This ether formation may be conducted, for example, using Mitsunobu conditions by reacting the phenol (X) with the protected aminocyclobutanol (XII) in the presence of diisopropylazodicarboxylate and triphenylphosphine in a suitable solvent such as tetrahydrofuran. Variants of the Mitsunobo reaction such as that described by Tsunoda (*Tetrahedron Letters*, 35, 5081, 1994) using cyanomethyenetributylphosphorane (CMBP) in toluene may also be used. The Mitsunobo reaction takes place with inversion of configuration such that if the input cyclobutanol (XII) has the trans configuration the product will have a cis configuration and if the input cyclobutanol (XII) has the cis configuration the product will have a trans configuration. Where the protecting group is a BOC group this can then be removed under acidic conditions, for example, using hydrochloric acid in dioxane, or TFA in dichloromethane to give compounds of formula (I) wherein X and Y are both hydrogen. This methodology may also be applicable to the preparation of compounds of formula (I) in which X or Y are a CH$_2$OH group but are likely to require additional protection of this primary hydroxyl group.

The compound of formula (XII) in which P is a BOC protecting group may be prepared by reaction of the amino alcohol (XIII),

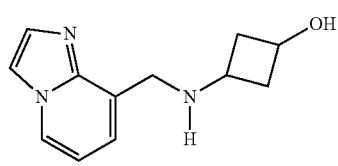

with bis(1,1-dimethylethyl)dicarbonate in the presence of a base such as triethylamine in a suitable solvent such as dichloromethane.

The compound of formula (XIII) may be prepared by reductive amination of the aldehyde (XIV),

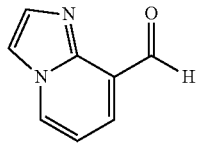

and an aminocyclobutanol of formula (XV),

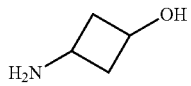

This reductive amination may be conducted, for example, using sodium triacetoxyborohydride as reducing agent in a suitable solvent, such as mixture of dichloromethane and methanol, at a suitable temperature, for example at room temperature. The coupling may also be conducted using alternative, conventional conditions for reductive amination known in the art.

The aldehyde (XIV) is known and is commercially available. The aminocyclopentanols of formula (XV) are known and are commercially available in racemic form and also as individual cis and trans isomers. The reductive amination reaction proceeds with retention of configuration such that starting with as aminocyclopentol gives the intermediate (XIII) also having the cis configuration.

A third process for the preparation of compounds of formula (I) comprises reduction of corresponding amides of formula (XVI),

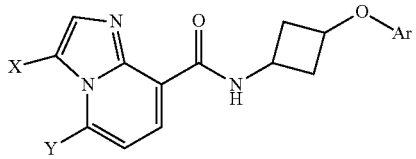

wherein X, Y and Ar are as defined above for compounds of formula (I). This reduction can be conducted using methodology described in the literature, for example using lithium borohydride in a suitable solvent such as tetrahydrofuran.

Amides of formula (XVI) may be prepared by coupling of carboxylic acids of formula (XVII), or activated derivatives thereof,

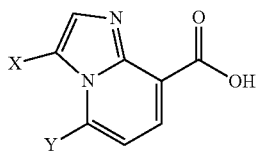

wherein X and Y are as defined above for compounds of formula (I) with a cyclobutylamine of formula (III),

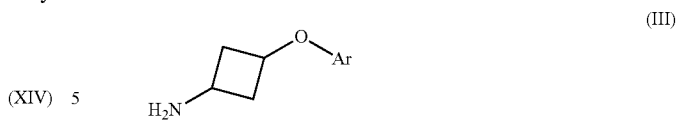

wherein Ar is as defined above for compounds of formula (I).

The amide coupling may be conducted using standard conditions reported in the literature. Where X or Y=CH$_2$OH this hydroxyl group may optionally be protected, for example as a MOM (methyoxymethyl)ether. This protecting group can be subsequently removed under acidic conditions.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with magnesium sulphate, or sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as methanol, ethanol, or butanol, or aqueous mixtures thereof. It will be appreciated that specific reaction times and temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives.

METHODS OF USE

In a further aspect, the invention provides a compound of formula (I) or a pharmaceutically acceptable salt thereof according to the first aspect of the invention for use in therapy Compounds of formula (I) and their pharmaceutically acceptable salts have TRPV1 antagonist activity and are believed to be of potential use for the treatment or prophylaxis of certain disorders, or treatment of the pain associated with them, such as: respiratory diseases, asthma, cough, COPD, bronchoconstriction, rhinitis, inflammatory disorders, pain, such as acute pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, oesophagitis, heart burn, Barrett's metaplasia, dysphagia, gastroeosophageal reflux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis andemesis, ocular disorders, dry eye disease.

Disorders of particular interest are respiratory diseases, asthma, cough, COPD, bronchoconstriction and inflammatory disorders.

In a further aspect the invention provides a compound of formula (I) or a pharmaceutically acceptable salt thereof according to the first aspect of the invention, for use in the treatment of a condition for which a TRPV1 antagonist is indicated.

In a further aspect the invention provides a compound of formula (I) or a pharmaceutically acceptable salt thereof according to the first aspect of the invention, for use in the treatment of rhinitis.

In a further aspect the invention provides a compound of formula (I) or a pharmaceutically acceptable salt thereof according to the first aspect of the invention, for use in the treatment of asthma.

In a further aspect the invention provides a compound of formula (I) or a pharmaceutically acceptable salt thereof according to the first aspect of the invention, for use in the treatment of cough.

In a further aspect the invention provides the use of a compound of formula (I) or a pharmaceutically acceptable salt thereof according to the first aspect of the invention in the manufacture of a medicament for the treatment of a condition for which a TRPV1 antagonist is indicated.

In a further aspect the invention provides the use of a compound of formula (I) or a pharmaceutically acceptable salt thereof according to the first aspect of the invention in the manufacture of a medicament for the treatment of rhinitis.

In a further aspect the invention provides the use of a compound of formula (I) or a pharmaceutically acceptable salt thereof according to the first aspect of the invention in the manufacture of a medicament for the treatment of asthma.

In a further aspect the invention provides the use of a compound of formula (I) or a pharmaceutically acceptable salt thereof according to the first aspect of the invention in the manufacture of a medicament for the treatment of cough.

In a further aspect the invention provides a method for the treatment or prophylaxis of disorders in which antagonism of TRPV1 is beneficial in a human comprising administering to the human in need thereof a therapeutically effective amount of a compound of formula (I) or a pharmaceutically acceptable salt thereof according to the first aspect of the invention.

In a further aspect the invention provides a method for the treatment of rhinitis in a human in need thereof comprising administering to the human a therapeutically effective amount of a compound of formula (I) or a pharmaceutically acceptable salt thereof according to the first aspect of the invention.

In a further aspect the invention provides a method for the treatment of asthma in a human in need thereof comprising administering to the human a therapeutically effective amount of a compound of formula (I) or a pharmaceutically acceptable salt thereof according to the first aspect of the invention.

In a further aspect the invention provides a method for the treatment of cough in a human in need thereof comprising administering to the human a therapeutically effective amount of a compound of formula (I) or a pharmaceutically acceptable salt thereof according to the first aspect of the invention.

COMPOSITIONS

For use in this invention a compound of formula (I) or a pharmaceutically acceptable salt thereof may be formulated with one or more pharmaceutically acceptable excipients to provide a pharmaceutical composition.

Thus, in a further aspect, the invention provides a pharmaceutical composition comprising a compound of formula (I) or a pharmaceutically acceptable salt thereof according to the first aspect of the invention and one or more pharmaceutically acceptable carriers or excipients.

In a further aspect there is provided a pharmaceutical composition for the treatment or prophylaxis of disorders in which antagonism of TRPV1 is beneficial comprising a compound as defined in the first aspect of the present invention or a pharmaceutically acceptable salt thereof and a pharmaceutically acceptable carrier.

In a further aspect there is provided a pharmaceutical composition for the treatment or prophylaxis of rhinitis comprising a compound as defined in the first aspect of the present invention or a pharmaceutically acceptable salt thereof and a pharmaceutically acceptable carrier.

In a further aspect there is provided a pharmaceutical composition for the treatment or prophylaxis of asthma comprising a compound as defined in the first aspect of the present invention or a pharmaceutically acceptable salt thereof and a pharmaceutically acceptable carrier.

In a further aspect there is provided a pharmaceutical composition for the treatment or prophylaxis of cough comprising a compound as defined in the first aspect of the present invention or a pharmaceutically acceptable salt thereof and a pharmaceutically acceptable carrier. For use in this invention a compound of formula (I) or a pharmaceutically acceptable salt thereof would typically be in a particle-size-reduced form, which may be prepared by conventional techniques, for example, microfluidisation, micronisation and milling e.g. wet bead milling. Generally, the size-reduced (e.g. micronised) compound of formula (I) or a pharmaceutically acceptable salt thereof can be defined by a $D_{50}$ value of about 0.1 to 10 microns such as about 0.5 to 10 microns, more particularly about 2 to 4 microns (for example as measured using laser diffraction).

The proportion of a compound of formula (I) or a pharmaceutically acceptable salt thereof will depend on the precise type of composition to be prepared, but will generally be within the range of from about 0.01 to 20% (w/w), based on the total weight of the composition. Generally, however for most types of preparations the proportion used will be within the range of from about 0.05 to 10% (w/w), such as about 0.1 to 5% (w/w).

The dose of a compound of formula (I) or a pharmaceutically acceptable salt thereof will vary in the usual way with the seriousness of the disease to be treated and other factors such as the weight of the sufferer. As a general guide suitable unit doses for intranasal or inhaled use may be about between 0.005 and 1 mg for example between 0.005 and 0.5 mg per dose. Such unit doses may be administered once a day, or more than once a day, for example two or three times a day. Such therapy may extend for a number of weeks or months.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment, the invention provides a formulation for intranasal administration comprising a compound of formula (I) or a pharmaceutically acceptable salt thereof.

In a further aspect of the present invention, there is provided an aqueous pharmaceutical composition comprising a compound of formula (I) or a pharmaceutically acceptable salt thereof, in particular a composition adapted for intranasal administration.

The aqueous pharmaceutical composition of the invention may be in the form of an aqueous suspension or an aqueous solution. In one embodiment, the aqueous pharmaceutical composition of the invention is in the form of an aqueous suspension.

In one aspect of the present invention, there is provided a pharmaceutical composition comprising a compound of formula (I) or a pharmaceutically acceptable salt thereof, in particular a composition adapted for oral administration.

Pharmaceutical compositions adapted for oral administration may be presented as discrete units such as tablets or capsules; powder or granules; solutions or suspensions in aqueous or non-aqueous liquids; edible foams or whips; or oil-in-water liquid emulsions or water-in-oil emulsions Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

In a further aspect of the present invention, there is provided a pharmaceutical composition comprising a compound of formula (I) or a pharmaceutically acceptable salt thereof, in particular a composition adapted for inhaled or intranasal administration.

Compositions for inhaled or intranasal administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

The compounds of the invention may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. The compound(s) of the invention and the other pharmaceutically active agent(s) may be administered together in a single pharmaceutical composition or separately and, when administered separately this may occur simultaneously or sequentially in any order wherein one treatment agent is administered first and the other second or vice versa. Such sequential administration may be close in time or remote in time.

Thus the invention includes in a further aspect a combination comprising a compound of formula (I), or a pharmaceutically acceptable salt thereof, together with at least one other therapeutically active agent.

The amounts of the compound(s) of the invention and the other pharmaceutically active agent(s) and the relative timings of administration will be selected in order to achieve the desired combined therapeutic effect.

It will be appreciated that when the compound of the present invention is administered in combination with one or more other therapeutically active agents normally administered by the inhaled, intravenous, oral, intranasal or other route, that the resultant pharmaceutical composition may be administered by the same route. Alternatively, the individual components of the composition may be administered by different routes.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, antihistamines, steroids, NSAIDs, leukotriene modulators (e.g. montelukast) iNOS inhibitors, tryptase inhibitors, IKK2 inhibitors, p38 inhibitors, Syk inhibitors, elastase inhibitors, beta-2 integrin antagonists, adenosine a2a agonists, chemokine antagonists such as CCR3 antagonists or CCR4 antagonists, mediator release inhibitors such as sodium chromoglycate, 5-lipoxygenase inhibitors, DP1 antagonists, DP2 antagonists, p3K delta inhibitors, ITK inhibitors, LP (lysophosphatidic) inhibitors or FLAP (5-lipoxygenase activating protein) inhibitors (sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate) bronchodilators (e.g. beta-2 agonists, adrenergic agonists, anticholinergic agents, theophylline), methotrexate, and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

Aqueous pharmaceutical compositions according to the invention can be prepared using standard procedures that are familiar to the person skilled in the art e.g. by admixture of the various components, suitably at ambient temperature and atmospheric pressure.

In one embodiment, the aqueous pharmaceutical compositions of the invention are suitable for intranasal administration.

Where the composition is an aqueous pharmaceutical composition, optionally a further active ingredient may be incorporated into the aqueous pharmaceutical composition, particularly one used in the treatment of rhinitis and suitable for intranasal administration such as an anti-histamine or a corticosteroid.

For use in combination, suitable examples of anti-histamines include azelastine, olopatadine, bepotastine or a compound selected from:

N-[2-((2R)-2-{[4-[(4-chlorophenyl)methyl]-1-oxo-2(1H)-phthalazinyl]methyl}-1-pyrrolidinyl)ethyl]-4-(methyloxy)butanamide (as disclosed in patent application WO2008/74803);

4-[(4-chlorophenyl)methyl]-2-({(2R)-1-[4-(4-{[3-(hexahydro-1H-azepin-1-yl)propyl]oxy}phenyl) butyl]-2-pyrrolidinyl}methyl)-1(2H)-phthalazinone (as disclosed in patent application WO2007/122156); or N-(4-{4-[(6-butyl-8-quinolinyl)oxy]-1-piperidinyl}butyl) ethanesulfonamide (as disclosed in patent application PCT/EP2008/060622, published as WO2009/021965).

For use in combination, suitable examples of corticosteroids include fluticasone propionate (which is marketed as an intranasal formulation under the trade name Flixonase®), beclomethasone dipropionate (which is marketed as an intranasal formulation under the trade name Beconase®) or fluticasone furoate (which is marketed under the trade name Veramyst®). In one embodiment the present invention provides for an aqueous pharmaceutical composition comprising a compound of formula (I) or a pharmaceutically acceptable salt thereof and fluticasone furoate.

When present the proportion of the further active ingredient will generally be in the range from about 0.05 to 10% (w/w), such as about 0.1 to 5% (w/w).

ABBREVIATIONS

The following list provides definitions of certain abbreviations as used herein. It will be appreciated that the list is not exhaustive, but the meaning of those abbreviations not herein below defined will be readily apparent to those skilled in the art.

DCM Dichloromethane
DIPEA Diisopropylethylamine
DMF N,N-Dimethylformamide
DMSO Dimethylsulphoxide
DME 1,2-Dimethoxyethane
THF Tetrahydrofuran
EtOAc Ethyl acetate
MeOH Methanol
EtOH Ethanol
MeCN Acetonitrile
TBME tert-Butyl methy ether
HCl Hydrochloric acid
HPLC High performance liquid chromatography
MDAP Mass Directed Autopreparative HPLC
SPE Solid phase extraction
MeOH Methanol
TFA Trifluoroacetic acid
DIPEA N,N-Diisopropylethylamine
HATU O-(7-Azabenzotriazol-1-yl)-N,N,N',N'-tetramethyluronium hexafluorophosphate

EXPERIMENTAL DETAILS

NMR $^1$H NMR spectra were recorded in either CDCl$_3$, DMSO-d$_6$ or methanol-d$_4$ on either a Bruker DPX 400 or Bruker Avance DRX or Varian Unity 400 spectrometer all working at 400 MHz. The internal standard used was either tetramethylsilane or the residual protonated solvent at 7.25 ppm for CDCl$_3$, 2.50 ppm for DMSO-d$_6$ or 3.31 ppm for methanol-d$_4$.

LCMS

System A
Column: 50 mm×2.1 mm ID, 1.7 μm Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 0.1% v/v formic acid in water
B: 0.1% v/v formic acid acetonitrile

|  | Time (min.) | A % | B % |
|---|---|---|---|
| Gradient: | 0 | 97 | 3 |
|  | 1.5 | 0 | 100 |
|  | 1.9 | 0 | 100 |
|  | 2.0 | 97 | 3 |

System B
Column: 50 mm×4.6 mm ID, 3.5 μm XBridge C$_{18}$ column
Flow Rate: 3 mL/min.
Temp: 30° C.
UV detection range: 210 to 350 nm
Mass spectrum: Recorded on a mass spectrometer using alternative-scan positive and negative mode electrospray ionisation
Solvents: A: 10 mM ammonium bicarbonate in water adjusted to pH10 with ammonia solution
B: acetonitrile

|  | Time (min.) | A % | B % |
|---|---|---|---|
| Gradient: | 0 | 99 | 1 |
|  | 0.1 | 99 | 1 |
|  | 4.0 | 3 | 97 |
|  | 5.0 | 3 | 97 |

System C
Column: 50 mm×2.1 mm ID, 1.7 μm Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 10 mM ammonium bicarbonate in water adjusted to pH10 with ammonia solution
B: acetonitrile

|  | Time (min.) | A % | B % |
|---|---|---|---|
| Gradient: | 0 | 99 | 1 |
|  | 1.5 | 3 | 97 |
|  | 1.9 | 3 | 97 |
|  | 2.0 | 0 | 100 |

Mass Directed Autopreparative HPLC (MDAP)

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method

Conducted on an XBridge $C_{18}$ column (typically 150 mm×19 mm i.d. 5 µm packing diameter) at ambient temperature. The solvents employed were:

A=10 mM aqueous ammonium bicarbonate adjusted to pH 10 with ammonia solution.

B=acetonitrile.

PREPARATION OF INTERMEDIATES

Intermediate 1: Methyl 5-chloroimidazol[1,2-a]pyridine-8-carboxylate

To a stirred suspension of methyl 2-amino-6-chloro-3-pyridinecarboxylate (2 g, 10.72 mmol) and sodium bicarbonate (900 mg, 10.72 mmol) in a mixture of methanol (40 mL) and water (20 mL) was added chloroacetaldehyde (50% wt. solution in water, 2.9 mL, 22.51 mmol). The resultant mixture was heated at reflux for 5 hours when more chloroacetaldehyde (50% wt. solution in water, 1.45 mL, 11.25 mmol) was added and heating at reflux continued for 16 hours. The majority of the solvent was then removed in vacuo and the residue was partitioned between ethyl acetate (150 mL) and saturated aqueous sodium bicarbonate (150 mL). The organic phase was separated and the aqueous phase was back extracted with ethyl acetate (150 mL). The combined organic extracts were dried ($MgSO_4$), filtered and concentrated in vacuo. The residue was dissolved in DCM and purified on a silica cartridge (100 g) using a 0-100% ethyl acetate-cyclohexane+0-20% methanol gradient over 60 mins. The appropriate fractions were combined and evaporated in vacuo to give the title compound as a yellow solid (1.32 g).

LCMS (System A): $t_{RET}$=0.34 min; $MH^+$211, 213

Intermediate 2: Ethyl 3-(hydroxymethyl)imidazo[1,2-a]pyridine-8-carboxylate

A mixture of ethyl imidazo[1,2-a]pyridine-8-carboxylate (1 g, 5.26 mmol), sodium acetate (1.725 g, 21.03 mmol), formaldehyde (36.5% wt. in water, 2.5 mL, 33.1 mmol) and acetic acid (1.145 mL, 20 mmol) was stirred at room temperature for 3 hours. The reaction mixture was then heated at reflux for a further 4 hours and then cooled and diluted with water (50 mL). The pH was adjusted to 8 with saturated aqueous sodium hydrogen carbonate solution (ca. 10 mL) and the solution was extracted successively with ethyl acetate (3×50 mL) and 3:1 chloroform:isopropanol (100 mL). The organic extracts were combined, washed successively with saturated sodium bicarbonate (50 mL) and brine (50 mL) and dried ($MgSO_4$), filtered and the solvent evaporated in vacuo. The residue was dissolved in dichloromethane and purified on a silica cartridge (100 g) using a 0-30% methanol (+1% $Et_3N$)-DCM gradient over 60 mins. The product containing fractions were combined and evaporated in vacuo to give the title compound as a colourless oil (1.007 g)

LCMS (System A): $t_{RET}$=0.36 min; $MH^+$221

Intermediate 3: Ethyl 3-({[(1,1-dimethylethyl)(diethyl)silyl]oxy}methyl)imidazo[1,2-a]pyridine-8-carboxylate To a stirred solution of ethyl 3-(hydroxymethyl)imidazo[1,2-a]pyridine-8-carboxylate (2.7 g, 12.26 mmol) in DCM (100 mL) under nitrogen was added tert-butylchlorodimethyl silane (4 g, 26.5 mmol), 4-dimethylamino pyridine (0.32 g, 2.62 mmol) and triethylamine (3 mL, 21.52 mmol) and the reaction mixture heated at 50° C. under nitrogen for 16 hours. The mixture was concentrated in vacuo and the residue was dissolved in DCM and purified on a silica cartridge (100 g) using a 0-30% methanol-DCM gradient over 60 mins. The product containing fractions were combined and evaporated in vacuo to give the title compound as an off-white solid (4.174 g).

LCMS (System A): $t_{RET}$=0.94 min; $MH^+$335

Intermediate 4: cis-3-Aminocyclobutanol, hydrochloride 1,1-dimethylethyl(cis-3-hydroxycyclobutyl)carbamate (3 g, 16.02 mmol) was stirred in HCl in diethyl ether (2M, 45 ml, 90 mmol) over the weekend. TLC (10% MeOH in DCM, visualisation with $KMnO_4$ dip) showed no starting material remained. The reaction was concentrated in vacuo (water bath at ambient temperature). The crude material was washed with diethyl ether (40 mL) to afford the title compound.

$^1$H NMR (400 MHz, Methanol-$d_4$) δ ppm 1.97-2.09 (m, 2H) 2.65-2.75 (m, 2H) 3.25-3.37 (m, 2H) 4.01-4.11 (m, 1H)

Intermediate 5: cis-3-[(Imidazo[1,2-a]pyridin-8-ylmethyl)amino]cyclobutanol

To an emulsion of cis-3-aminocyclobutanol hydrochloride (1.254 g, 10.15 mmol) in DCM (15 mL) was added MeOH (60 mL), imidazo[1,2-a]pyridine-8-carbaldehyde (1.5 g, 10.26 mmol) and DIPEA (2 mL, 11.45 mmol) and the reaction mixture stirred at room temperature under nitrogen for 10 minutes. Sodium triacetoxyborohydride (5.4 g, 25.5 mmol) was then added and the reaction mixture stirred under nitrogen for 18 hours and then concentrated in vacuo. The residue was dissolved in DCM (200 mL), aqueous sodium hydroxide (2M, 200 mL) was added and the mixture was stirred at room temperature for 1 hour. The layers were separated and to the aqueous phase was added sodium hydroxide pellets (ca. 5 g) which was then extracted with 3:1 chloroform:isopropanol (2×500 mL). The combined organic extracts were dried using a hydrophobic frit, evaporated in vacuo and the residue was dissolved in DCM and purified on a silica cartridge (100 g) using a 0-25% methanol-DCM gradient over 60 min. The product containing fractions were combined and evaporated in vacuo to give the title compound as an orange oil (2.3 g).

LCMS (System B): $t_{RET}$=1.33 min; $MH^+$ 218

Intermediate 6: 1,1-Dimethylethyl(cis-3-hydroxycyclobutyl)(imidazo[1,2-a]pyridin-8-ylmethyl)carbamate To a solution of cis-3-[(imidazo[1,2-a]pyridin-8-ylmethyl)amino]cyclobutanol (1.809 g, 8.33 mmol) and triethylamine (1.625 mL, 11.66 mmol) in DCM (50 mL) was added bis(1,1-dimethylethyl)dicarbonate (1.908 g, 8.74 mmol) and the mixture stirred at room temperature for 18 hours under nitrogen. The mixture was then concentrated in vacuo and the residue was dissolved in DCM and purified on a silica cartridge (100 g) using a 0-15% methanol(+1% Et$_3$N)-DCM gradient over 60 min. The product containing fractions were combined and evaporated in vacuo to give the title compound as a white solid (2.246 g).

LCMS (System B): t$_{RET}$=2.14 min; MH$^+$318

Intermediate 7: 1,1-Dimethylethyl {cis-3-[(2,3-dichlorophenyl)oxy]cyclobutyl}carbamate To a stirred mixture of 2,3-dichlorophenol (4.35 g, 26.7 mmol), polymer bound triphenylphosphine (13.35 g, 40.1 mmol) and 1,1-dimethylethyl(trans-3-hydroxycyclobutyl)carbamate (5 g, 26.7 mmol) in anhydrous THF (250 mL) at ambient temperature was added neat diisopropylazodicarboxylate (7.79 mL, 40.1 mmol). The reaction mixture was warmed to 50° C. under a nitrogen atmosphere for 18 hours and then cooled and filtered through a plug of celite (10 g). The filtrate was concentrated in vacuo to give a viscous oil (22 g) which was dissolved in DCM (250 mL) and washed with 2M aqueous sodium hydroxide (250 mL). The aqueous layer was re-extracted with DCM (250 mL) and the combined organic extracts were dried using a hydrophobic frit and concentrated in vacuo. The residue (ca. 21 g) was pre-absorbed on florosil and purified on silica gel cartridges (3×100 g) using a 0-25% ethyl acetate-cyclohexane gradient over 40 min. The product containing fractions were combined and evaporated in vacuo to give the title compound as a white solid (5.21 g).

$^1$H NMR (400 MHz, Methanol-d$_4$) δ ppm 1.43 (s, 9H) 2.02-2.12 (m, 2H) 2.85-2.94 (m, 2H) 3.73-3.86 (m, 1H) 4.43-4.52 (m, 1H) 6.87 (dd, J=8.3, 1.3 Hz, 1H) 7.06-7.10 (m, 1H) 7.15-7.21 (m, 1H).

Intermediate 8: cis-3-[(2,3-Dichlorophenyl)oxy]cyclobutanamine, hydrochloride

To 1,1-dimethylethyl {cis-3-[(2,3-dichlorophenyl)oxy]cyclobutyl}carbamate (5.21 g, 15.68 mmol) was added hydrochloric acid in dioxane (4M, 40 mL, 160 mmol) and the reaction mixture stirred in a sealed vessel at room temperature for 1 hour. The mixture was diluted with dioxane (300 mL) and stirred for a further 5 hours. Diethyl ether (300 mL) was then added and the solid collected by filtration and dried under high vacuum overnight to give the title compound (4.149 g)

$^1$H NMR (400 MHz, Methanol-d$_4$) δ ppm 2.28-2.38 (m, 2H) 2.98-3.08 (m, 2H) 3.56 (t, J=8.0 Hz, 1H) 3.65 (s, 2H) 4.67 (t, J=7.0 Hz, 1H) 6.88 (dd, J=8.3, 1.3 Hz, 1H) 7.12-7.16 (m, 1H) 7.19-7.25 (m, 1H)

Intermediate 9: 1,1-Dimethylethyl(trans-3-{[4-(1,1-dimethylethyl)-3,5-difluorophenyl]oxy}cyclobutyl)carbamate To a stirred solution of 4-(1,1-dimethylethyl)-3,5-difluorophenol (2.4 g, 12.89 mmol), triphenylphosphine (4.20 g, 16.02 mmol) and 1,1-dimethylethyl(cis-3-hydroxycyclobutyl)carbamate (2 g, 10.68 mmol) in anhydrous THF (100 mL) at ambient temperature was added neat diisopropylazodicarboxylate (3.12 mL, 16.02 mmol). The reaction was warmed to 45° C. under a nitrogen atmosphere for 23.5 hours. The solvent was evaporated in vacuo and the residue taken up in DCM (75 mL), washed with aqueous 2M sodium hydroxide (75 mL) dried using a hydrophobic frit and the solvent evaporated in vacuo. The residue was dissolved in DCM and purified in two batches on silica cartridges (2×100 g) using a gradient of 0-25% ethyl acetate-cyclohexane over 60 min. The appropriate fractions were combined and evaporated in vacuo to give the title compound as a white solid (3.08 g).

$^1$H NMR (400 MHz, CDCl$_3$) δ ppm 1.36-1.55 (m, 18H) 2.31-2.45 (m, 2H) 2.49-2.62 (m, 2H) 4.19-4.37 (m, 1H) 4.65-4.82 (m, 1H) 6.18-6.28 (m, 2H).

Intermediate 10: trans-3-{[4-(1,1-dimethylethyl)-3,5-difluorophenyl]oxy}cyclobutanamine 1,1-dimethylethyl(trans-3-{[4-(1,1-dimethylethyl)-3,5-difluorophenyl]oxy}cyclobutyl)carbamate (257 mg, 0.723 mmol) was stirred in 4M HCl in dioxane (5 mL, 20 mmol) overnight and then concentrated in vacuo and loaded onto an SCX cartridge (10 g) and eluted with MeOH (3 column volumes) and then flushed with ammonia in MeOH. Concentration of the product containing fractions in vacuo gave the title compound (142.3 mg).

$^1$H NMR (400 MHz, Methanol-d$_4$) δ ppm 1.35-1.44 (m, 9H) 2.51-2.73 (m, 4H) 3.92-4.03 (m, 1H) 4.89-4.97 (m, 1H) 6.31-6.40 (m, 2H).

Intermediate 11: 1,1-Dimethylethyl(cis-3-{[4-(1,1-dimethylethyl)-3,5-difluorophenyl]oxy}cyclobutyl)carbamate To a stirred solution of 4-(1,1-dimethylethyl)-3,5-difluorophenol (4.97 g, 26.7 mmol), polymer bound triphenylphosphine (13.35 g, 40.1 mmol) and 1,1-dimethylethyl(trans-3-hydroxycyclobutyl)carbamate (5 g, 26.7 mmol) in anhydrous THF (250 mL) at ambient temperature was added neat diisopropylazodicarboxylate (7.79 mL, 40.1 mmol). The reaction was warmed to 50° C. under a nitrogen atmosphere for 18 hours. The reaction was vacuum filtered through a plug of celite (10 g) and the filtrate concentrated in vacuo to give 19.8 g of viscous oil. The oil was taken up in ethyl acetate (400 mL) and washed with 2M aqueous sodium hydroxide (400 mL). The resultant organic layer was dried (MgSO$_4$), filtered and concentrated in vacuo to give an oil (18.6 g) which solidified on standing. Trituration was attempted with diethyl ether (ca. 200 mL); the resulting solid was collected by filtration and dried in vacuo (0.27 g) and the filtrate was concentrated in vacuo to give an oil (17.8 g). The oil was loaded in DCM and purified by chromatography on silica (2×100 g cartridges) eluting with a gradient of 0-25% ethyl acetate-cyclohexane over 60 mins. The appropriate fractions were combined and evaporated in vacuo to give the title compound as a white solid (6.90 g)

$^1$H NMR (400 MHz, CDCl$_3$) δ ppm 1.38-1.52 (m, 18H) 1.94-2.04 (m, 2H) 2.88-3.00 (m, 2H) 3.84-3.99 (m, 1H) 4.29 (s, 1H) 4.63-4.76 (m, 1H) 6.26 (d, J=12.5 Hz, 2H)

Intermediate 12: cis-3-{[4-(1,1-dimethylethyl)-3,5-difluorophenyl]oxy}cyclobutanamine, hydrochloride To a stirred solution of 1,1-dimethylethyl(cis-3-{[4-(1,1-dimethylethyl)-3,5-difluorophenyl]oxy}cyclobutyl)carbamate (6.85 g, 19.27 mmol) in 1,4-dioxane (50 mL) was added a solution of hydrogen chloride in 1,4-dioxane (50 mL, 4M, 200 mmol) in one charge. The reaction vessel was sealed and the reaction stirred at ambient temperature for 16 hours. The reaction was concentrated to approximately half volume in vacuo and the resultant slurry was diluted with diethyl ether (200 mL) and the mixture stirred rapidly for 10 min. The precipitate was collected by filtration and dried in vacuo to give the title compound as a white solid (3.39 g). The mother liquors were concentrated in vacuo to give a yellow sticky solid. Trituration with diethyl ether (ca 20 mL) gave a white precipitate, the precipitate was collected by filtration and dried in vacuo to give a further batch of the title compound (1.035 g).

$^1$H NMR (400 MHz, Methanol-d$_4$) δ ppm 1.41 (t, 9H) 2.19-2.30 (m, 2H) 2.97 (d, J=7.0 Hz, 2H) 3.55 (s, 1H) 4.56 (s, 1H) 6.40 (d, J=-12.8 Hz, 2H)

Intermediate 13: 1,1-Dimethylethyl{trans-3-[(2,3-dichlorophenyl)oxy]cyclobutyl}carbamate To a stirred solution of 2,3-dichlorophenol (2.1 g, 12.88 mmol), 1,1-dimethylethyl(cis-3-hydroxycyclobutyl)carbamate (2 g, 10.68 mmol) and triphenylphosphine (4.2 g, 16.02 mmol) in THF (100 mL) was added diisopropyl azodicarboxylate (3.12 mL, 16.02 mmol) and the mixture stirred under nitrogen at 50° C. for 16 hours. The mixture was then concentrated in vacuo and the residue taken up in DCM (200 mL), washed with 2M aqueous sodium hydroxide (200 mL), dried using a hydrophobic frit and the solvent evaporated in vacuo. The residue was dissolved in DCM and purified on silica (2×100 g cartridges) using a 0-25% ethyl acetate-cyclohexane gradient over 60 min. The product containing fractions were combined and evaporated in vacuo to give the title compound as a white solid (3.323 g).

$^1$H NMR (400 MHz, DMSO-d$_6$) δ ppm 1.38 (s, 9H) 2.29-2.45 (m, 4H) 4.06-4.17 (m, 1H) 4.86-4.94 (m, 1H) 6.86-6.91 (m, 1H) 7.17-7.22 (m, 1H) 7.26-7.35 (m, 2H).

Intermediate 14: trans-3-[(2,3-Dichlorophenyl)oxy]cyclobutanamine, hydrochloride To 1,1-dimethylethyl {trans-3-[(2,3-dichlorophenyl)oxy]cyclobutyl}carbamate (10.78 g, 17.85 mmol) was added 4M hydrochloric acid in dioxane (150 mL, 600 mmol) and the reaction mixture stirred in a sealed vessel at room temperature for 18 hours. The mixture was then diluted with diethyl ether (300 mL), stirred for 10 min and then filtered and the solid dried in vacuo to give the title compound (4.4096 g).

$^1$H NMR (400 MHz, Methanol-d$_4$) δ 2.60-2.75 (m, 4H) 3.96-4.06 (m, 1H) 4.99-5.07 (m, 1H) 6.77-6.83 (m, 1H) 7.12-7.17 (m, 1H) 7.18-7.27 (m, 1H).

Intermediate 15: 1,1-Dimethylethyl(trans-3-{[4-fluoro-3-(trifluoromethyl)phenyl]oxy}cyclobutyl)carbamate Method A To a stirred suspension of 4-fluoro-3-(trifluoromethyl)phenol (2.365 g, 13.13 mmol), 1,1-dimethylethyl(cis-3-hydroxycyclobutyl)carbamate (2.2 g, 11.75 mmol) and polymer bound triphenylphosphine (5.87 g, 17.62 mmol) in dry THF (100 mL) was added neat diisopropyl azodicarboxylate (3.43 mL, 17.62 mmol) in one charge. The reaction was stirred at 50° C. for 22 hours. The reaction was filtered through a pad of celite and the cake washed with THF (100 mL). The filtrate was concentrated in vacuo and the residue dissolved in DCM (100 mL) and washed with 2M aqueous sodium hydroxide (100 mL). The organic phase was dried using a hydrophobic frit and concentrated in vacuo. The residue was purified by chromatography on silica (2×100 g) using a gradient of 0-50% ethyl acetate-cyclohexane gradient over 40 min. The appropriate fractions were combined and evaporated in vacuo to give the title compound as a white solid (3.17 g).

LCMS (System C): t$_{RET}$=3.43 min; MH$^-$ 348

$^1$H NMR (400 MHz, CDCl$_3$) δ ppm 1.46 (s, 9H) 2.35-2.46 (m, 2H) 2.50-2.61 (m, 2H) 4.24-4.37 (m, 1H) 4.71-4.81 (m, 1H) 6.87-6.99 (m, 2H) 7.06-7.14 (m, 1H)

Method B

A mixture of 1,1-dimethylethyl(cis-3-hydroxycyclobutyl)carbamate (3 g, 16.0 mmol), 4-fluoro-3-(trifluoromethyl)phenol (2.8 g, 16.02 mmol) and cyanomethylenetributylphosphorane (4.72 g, 19.56 mmol) in toluene (25 mL) was heated at 100° C. under nitrogen atmosphere for 4 hours and left standing overnight under a nitrogen atmosphere. The reaction mixture was then evaporated in vacuo to give a brown liquid (12 g). This material was loaded in DCM and purified by chromatography on silica (330 g) using 0-40% cyclohexane-TBME over 7 column volumes and then 40-60% cyclohexane-TBME over 1.5 column volumes and then 60% cyclohexane-TBME for 1.5 column volumes. The appropriate fractions were combined and evaporated in vacuo to give the title compound as an off-white solid (4.629 g) showing $^1$H NMR spectrum (400 MHz, CDCl$_3$) similar to that of material prepared by method A.

Intermediate 16: trans-3-{[4-Fluoro-3-(trifluoromethyl)phenyl]oxy}cyclobutanamine, hydrochloride To a stirred solution of 1,1-dimethylethyl(trans-3-{[4-fluoro-3-(trifluoromethyl)phenyl]oxy}cyclobutyl)carbamate (3.16 g, 9.05 mmol) in 1,4-dioxane (20 mL) was added hydrochloric acid in 1,4-dioxane (4M, 25 mL, 100 mmol) in one charge. The reaction vessel was sealed and the reaction stirred at ambient temperature for 16 hours. The majority of the solvent was then removed in vacuo leaving a slurry which was diluted with diethyl ether (ca 50 mL) and the solid collected by filtration and dried in vacuo to give the title compound (2.187 g).

LCMS (System B): T$_{RET}$=2.59 min; MH$^+$ 250

Intermediate 17: 1,1-Dimethylethyl(imidazo[1,2-a]pyridin-8-ylmethyl)(trans-3-{[3-(trifluoromethyl)phenyl]oxy}cyclobutyl)carbamate To a solution of 1,1-dimethylethyl(cis-3-hydroxycyclobutyl)(imidazo[1,2-a]pyridin-8-ylmethyl)carbamate (80 mg, 0.252 mmol), 3-(trifluoromethyl)phenol (40.9 mg, 0.252 mmol) and triphenyl phosphine (99 mg, 0.378 mmol) in anhydrous THF (3 mL) was added diisopropyl azodicarboxylate (0.074 mL, 0.378 mmol) and the reaction stirred at 50° C. under nitrogen over the weekend. LCMS indicated the reaction to be incomplete and more diisopropyl azodicarboxylate (0.074 mL, 0.378 mmol) was added and the reaction left to stir at 50° C. for 2 hours. The cooled reaction mixture was evaporated in-vacuo and the residue partitioned between DCM and 2M aqueous sodium hydroxide solution. The organic layer was passed through a hydrophobic frit and evaporated in-vacuo to yield a yellow oil which was dissolved in 50:50 DMSO/MeOH (3 mL) and purified by MDAP (3 injections). Product containing fractions were combined and concentrated to give the title compound (48.2 mg).

LCMS (System B): t$_{RET}$=3.47 min; MH$^+$ 462

Intermediate 18: 1,1-Dimethylethyl{trans-3-[(2,3-dichlorophenyl)oxy]cyclobutyl}(imidazo[1,2-a]pyridin-8-ylmethyl)carbamate To a stirred solution of 1,1-dimethylethyl(cis-3-hydroxycyclobutyl)(imidazo[1,2-a]pyridin-8-ylmethyl)carbamate (80 mg, 0.252 mmol), 2,3-dichlorphenol (41.1 mg, 0.252 mmol) and triphenylphosphine (100 mg, 0.381 mmol) in anhydrous THF (3 mL) at ambient temperature was added neat diisopropylazodicarboxylate (0.075 mL, 0.386 mmol) and the reaction heated to 50° C. for 16 hours. The reaction was concentrated in vacuo and the residue was dissolved in DCM (10 mL) and washed with 2M aqueous sodium hydroxide (10 mL). The organic phase was separated and dried (hydrophobic frit) and then concentrated in vacuo. The residue (300 mg) was dissolved in DCM and purified on a silica cartridge (10 g) using a 0-25% methanol-DCM gradient over 30 min. The product containing fractions were combined and evaporated in vacuo to give material still contaminated with triphenylphosphine oxide. This material was dissolved in 1:1 MeOH:DMSO (3 mL) and re-purified by MDAP (3 injections). Product containing fractions were combined and evaporated under a stream of nitrogen to give the title compound (56 mg).

LCMS (System B): $t_{RET}$=3.54 min; MH$^+$462, 464, 466

Intermediate 19: 1,1-Dimethylethyl(trans-3-{[2-chloro-3-(trifluoromethyl)phenyl]oxy}cyclobutyl)(imidazo[1,2-a]pyridin-8-ylmethyl)carbamate Prepared similarly to Intermediate 17 from 1,1-dimethylethyl(cis-3-hydroxycyclobutyl)(imidazo[1,2-a]pyridin-8-ylmethyl)carbamate and 2-chloro-3(trifluoromethyl)phenol but stirred overnight at 50° C. after the first addition of diisopropylazodicarboxylate and for 1 hour at 50° C. after the second addition.

LCMS (System B): $t_{RET}$=3.56 min; MH$^+$496, 498

Intermediate 20: 1,1-Dimethylethyl(trans-3-{[4-chloro-3-(trifluoromethyl)phenyl]oxy}cyclobutyl)(imidazo[1,2-a]pyridin-8-ylmethyl)carbamate Prepared similarly to Intermediate 19 from 1,1-dimethylethyl(cis-3-hydroxycyclobutyl)(imidazo[1,2-a]pyridin-8-ylmethyl)carbamate and 4-chloro-3(trifluoromethyl)phenol.

LCMS (System B): $t_{RET}$=3.65 min; MH$^+$496, 498

Intermediate 21: 1,1-Dimethylethyl(trans-3-{[4-fluoro-3-(trifluoromethyl)phenyl]oxy}cyclobutyl)(imidazo[1,2-a]pyridin-8-ylmethyl)carbamate Prepared similarly to Intermediate 17 from 1,1-dimethylethyl(cis-3-hydroxycyclobutyl)(imidazo[1,2-a]pyridin-8-ylmethyl)carbamate and 4-fluoro-3(trifluoromethyl)phenol.

LCMS (System B): $t_{RET}$=3.49 min; MH$^+$480

Intermediate 22: 1,1-Dimethylethyl(trans-3-{[2-chloro-4-(trifluoromethyl)phenyl]oxy}cyclobutyl)(imidazo[1,2-a]pyridin-8-ylmethyl)carbamate Prepared similarly to Intermediate 19 from 1,1-dimethylethyl(cis-3-hydroxycyclobutyl)(imidazo[1,2-a]pyridin-8-ylmethyl)carbamate and 2-chloro-4(trifluoromethyl)phenol but with reaction for 4 hours at 50° C. after the second addition of diisopropylazodicarboxylate.

LCMS (System B): $t_{RET}$=3.66 min; MH$^+$ 496, 498

Intermediate 23: 1,1-Dimethylethyl(trans-3-{[4-chloro-2-(trifluoromethyl)phenyl]oxy}cyclobutyl)(imidazo[1,2-a]pyridin-8-ylmethyl)carbamate Prepared similarly to Intermediate 19 from 1,1-dimethylethyl(cis-3-hydroxycyclobutyl)(imidazo[1,2-a]pyridin-8-ylmethyl)carbamate and 4-chloro-2(trifluoromethyl)phenol but without the addition of a second aliquot of diisopropylazodicarboxylate.

LCMS (System B): $t_{RET}$=3.67 min; MH$^+$ 496, 498

Intermediate 24: 1,1-Dimethylethyl(trans-3-{[3-chloro-5-(trifluoromethyl)phenyl]oxy}cyclobutyl)(imidazo[1,2-a]pyridin-8-ylmethyl)carbamate Prepared similarly to Intermediate 22 from 1,1-dimethylethyl(cis-3-hydroxycyclobutyl)(imidazo[1,2-a]pyridin-8-ylmethyl)carbamate and 3-chloro-5(trifluoromethyl)phenol.

LCMS (System B): $t_{RET}$=3.76 min; MH$^+$ 496, 498

Intermediate 25: trans-3-[(2,3-Dichlorophenyl)oxy]-N-{[5-({[(methyloxy)methyl]oxy}methyl)imidazo[1,2-a]pyridin-8-yl]methyl}cyclobutanamine To a suspension of methyl 5-chloroimidazo[1,2-a]pyridine-8-carboxylate (1.115 g, 5.29 mmol) and tributyl({[(methyloxy)methyl]oxy}methyl)stannane (2.03 g, 5.56 mmol) in anhydrous toluene (10 mL) was added chloro(di-2-norbonylphosphino)(2'-dimethylamino-1,1'-biphenyl-2-yl)palladium (II) (300 mg, 0.535 mmol). The reaction vessel was sealed and heated in a Biotage Initiator microwave using initial absorption setting high to 170° C. for 1 hour. After cooling the reaction was poured onto a biphasic mixture of ethyl acetate (100 mL) and an aqueous potassium floride solution (2 g in 100 mL). The mixture was stirred rapidly and filtered through a pad of celite (10 g). The biphasic filtrate was separated and the aqueous layer back extracted with ethyl acetate (2×100 mL). The combined organic extracts were dried (Na$_2$SO$_4$), filtered and concentrated in vacuo. The residue was dissolved in DCM and purified on a silica cartridge (100 g) using a 0-15% methanol-DCM gradient over 60 min. The appropriate fractions were combined and evaporated in vacuo to give impure material which was subjected to a second chromatographic purification on silica (100 g) using a 0-100% ethyl acetate-DCM gradient over 40 min followed by a 0-15% methanol-DCM gradient over 40 min. The appropriate fractions were combined and evaporated in vacuo to give still impure methyl 5-({[(methyloxy)methyl]oxy}methyl)imidazo[1,2-a]pyridine-8-carboxylate (302 mg, purity by LCMS/UV ca 65%) which was used directly in the next step.

To a stirred solution of sodium bis(2-methoxyethoxy)aluminium dihydride (65% wt. in toluene, 0.512 mL, 1.678 mmol) at 0° C. under a nitrogen atmosphere was added a solution of morpholine (0.147 mL, 1.678 mmol) in toluene (3.35 mL) dropwise over 15 min to give a solution of reducing agent (approx 4 mL, 4 eq). An aliquot of this solution (1.5 mL, ca 1.5 eq) was added dropwise over 2 min to a stirred solution of impure methyl 5-({[(methyloxy)methyl]oxy}methyl)imidazo[1,2-a]pyridine-8-carboxylate (105 mg, 0.420 mmol) in toluene (4 mL) at −40° C. The reaction was stirred at −40° C. for 40 min when LCMS indicated that the ester had been reduced to the aldehyde. The reaction was quenched carefully by addition of water (2 mL) and then allowed to warm to ambient temperature and concentrated in vacuo. The residue was pre-absorbed on florosil (100-200 mesh) and purified on a silica cartridge (20 g) using a 0-25% methanol-DCM gradient over 40 min. The appropriate fractions were combined and concentrated in vacuo to give impure 5-({[(methyloxy)methyl]oxy}methyl)imidazo[1,2-a]pyridine-8-carbaldehyde as a yellow oil (52 mg) which was used directly in the next step.

To a stirred solution of impure 5-({[(methyloxy)methyl]oxy}methyl)imidazo[1,2-a]pyridine-8-carbaldehyde (49 mg, 0.223 mmol) and trans-3-[(2,3-dichlorophenyl)oxy]cyclobutanamine hydrochloride salt (55 mg, 0.205 mmol) in a mixture of DCM (2 mL) and methanol (2 mL) was added DIPEA (0.039 mL, 0.223 mmol) and sodium triacetoxyborohydride (189 mg, 0.89 mmol). The reaction was stirred at ambient temperature for 3.5 hours when LCMS showed the reaction to be complete. DCM (10 mL) was added and the solution washed with saturated aqueous sodium bicarbonate (10 mL). The organic layer was dried (hydrophobic frit) and concentrated in vacuo. The residue was dissolved in DCM and purified on a silica cartridge (20 g) using a 0-10% methanol-DCM gradient over 40 min. The appropriate fractions were combined and evaporated in vacuo to give the title compound as a yellow oil (26 mg).

LCMS (System C): $t_{RET}$=1.20 min; MH$^+$ 436, 438, 440.

Intermediate 26: trans-3-{[4-Fluoro-3-(trifluoromethyl)phenyl]oxy}-N-{[5-({[(methyloxy)methyl]oxy}methyl)imidazo[1,2-a]pyridin-8-yl]methyl}cyclobutanamine To a stirred solution of 5-({[(methyloxy)methyl]oxy}methyl)imidazo[1,2-a]pyridine-8-carbaldehyde (34 mg, 0.154 mmol) and trans-3-{[4-fluoro-3-(trifluoromethyl)phenyl]oxy}cyclobutanamine hydrochloride salt (44 mg, 0.154 mmol) in a mixture of DCM (1 mL) and methanol (1 mL) was added DIPEA (0.027 mL, 0.155 mmol) and sodium triacetoxyborohydride (98 mg, 0.463 mmol). The reaction was stirred at ambient temperature for 3.5 hours and then diluted with DCM (10 mL). The solution was then washed with saturated aqueous sodium bicarbonate (10 mL), dried (hydrophobic frit) and concentrated in vacuo. The residue was dissolved in DCM and purified on a silica cartridge (10 g) using a 0-10% methanol-DCM gradient over 40 min. The product containing fractions were combined and evaporated in vacuo to give the title compound as a yellow oil (32 mg).

LCMS (System C): $t_{RET}$=1.19 min; MH$^+$ 454

Intermediate 27: trans-3-[(Imidazo[1,2-a]pyridin-8-ylmethyl)amino]cyclobutanol

To an emulsion of trans-3-aminocyclobutanol hydrochloride (287 mg, 2.322 mmol) in DCM (5 mL) was added methanol (20 mL), imidazo[1,2-a]pyridine-8-carbaldehyde (340 mg, 2.326 mmol) and diisopropylethylamine (0.446 mL, 2.55 mmol) and the reaction mixture was stirred at room temperature under nitrogen for 10 min. Sodium triacetoxyborohydride (1000 mg, 4.72 mmol) was then added and the reaction mixture was stirred under nitrogen for 2 hours when LCMS indicated the reaction to be complete. The reaction mixture was then concentrated in vacuo and the residue was taken up in DCM (200 mL) and aqueous 2M sodium hydroxide (200 mL) was added and the mixture was stirred at room temperature for 1 hour. The organic layer was separated, washed with water (2×200 mL) and the aqueous phase was back extracted using 3:1 chloroform:isopropanol (2×250 mL). The combined organic layers were dried using a hydrophobic frit and the solvent evaporated in vacuo. The residue was pre-absorbed on florosil and purified on a silica cartridge (100 g) using a 0-25% methanol-dichloromethane gradient over 60 min. The appropriate fractions were combined and evaporated in vacuo to give crude product still containing some borohydride residues. This material was dissolved in aqueous 2M sodium hydroxide (100 mL) and left at room temperature for 5 hours when sodium hydroxide pellets (ca. 0.5 g) was added and the mixture left at room temperature for a further 15 hours. The mixture was then extracted with 3:1 chloroform:isopropanol (2×300 mL) and the organic layer was separated, dried using a hydrophobic frit and the solvent evaporated in vacuo. The residue was dried on a high vacuum line for 2 hours to give the title compound as an orange oil (305 mg).

LCMS: (System B): $t_{RET}$=1.30 min; MH$^+$218

Intermediate 28: 1,1-Dimethylethyl(trans-3-hydroxycyclobutyl)(imidazo[1,2-a]pyridin-8-ylmethyl)carbamate Prepared similarly to Intermediate 6 from trans-3-[(imidazo[1,2-a]pyridin-8-ylmethyl)amino]cyclobutanol and bis(1,1-dimethylethyl)dicarbonate.

LCMS (System A): $t_{RET}$=0.45 min; MH$^+$318

Intermediate 29: 1,1-Dimethylethyl(cis-3-{[2-chloro-3-(trifluoromethyl)phenyl]oxy}cyclobutyl)(imidazo[1,2-a]pyridin-8-ylmethyl)carbamate Prepared similarly to Intermediate 18 from 1,1-dimethylethyl(trans-3-hydroxycyclobutyl)(imidazo[1,2-a]pyridin-8-ylmethyl)carbamate and 2-chloro-3-(trifluoromethyl)phenol. The crude product was purified by column chromatography on a silica cartridge (20 g) using a 0-100% EtOAc/cyclohexane gradient to give still impure title compound which was used without further purification.

LCMS (System C): $t_{RET}$=3.44 min; MH$^+$ 496, 498

Intermediate 30: 1,1-Dimethylethyl (cis-3-{[4-fluoro-3-(trifluoromethyl)phenyl]oxy}cyclobutyl)(imidazo[1,2-a]pyridin-8-ylmethyl)carbamate Prepared and purified similarly to Intermediate 29 from 1,1-dimethylethyl(trans-3-hydroxycyclobutyl)(imidazo[1,2-a]pyridin-8-ylmethyl)carbamate and 4-fluoro-3-(trifluoromethyl)phenol.

LCMS (System C): $t_{RET}$=3.40 min; MH$^+$ 480

Intermediate 31: Methyl 2-amino-6-({[(methyloxy)methyl]oxy}methyl)-3-pyridinecarboxylate To a degassed suspension of methyl 2-amino-6-chloro-3-pyridinecarboxylate (2.24 g, 12 mmol) and tributyl({[(methyloxy)methyl]oxy}methyl)stannane (4.82 g, 13.2 mmol) in anhydrous toluene (30 mL), split between two vessels, was added chloro(di-2-norbonylphosphino)(2'-dimethylamino-1,1'-biphenyl-2-yl)palladium (II) (325 mg, 0.598 mmol) to each vessel. The reaction vessels were sealed and heated in a Biotage Initiator using initial absorption normal to 170° C. for 1 hour. Analysis by LCMS indicated the reaction to be approximately 20-25% complete. The reaction was mixture was poured into a biphasic mixture of ethyl acetate (200 mL) and aqueous potassium flouride solution (3 g in 200 mL). The mixture was stirred rapidly for 10 min before filtering though celite (10 g). The filtrate was separated and the aqueous layer was back extracted with ethyl acetate (100 mL). The combined organic extracts were dried (Na$_2$SO$_4$), filtered and concentrated in vacuo. The residue was dissolved in toluene (30 mL) and treated again with tributyl({[(methyloxy)methyl]oxy}methyl)stannane (4.82 g, 13.2 mmol) and chloro(di-2-norbonylphosphino)(2'-dimethylamino-1,1'-biphenyl-2-yl)palladium (II) (0.67 g, 1.195 mmol). The resulting mixture was split into two and degassed. The reaction vessels were sealed and heated in a Biotage Initiator using initial absorption normal to 170° C. for 1 hour. Analysis by LCMS indicated all starting material had been consumed. The reaction mixture was poured into a biphasic mixture of ethyl acetate (200 mL) and aqueous potassium flouride solution (3 g in 200 mL). The mixture was stirred rapidly and then filtered through a pad of celite (10 g). The resultant biphasic filtrate was separated and the aqueous layer was back extracted with ethyl acetate (150 mL). The combined organic extracts were dried ($Na_2SO_4$), filtered and concentrated in vacuo to give a yellow slurry. This material was dissolved in DCM/methanol and purified by SPE on a sulphonic acid cartridge (SCX, 50 g) using first DCM/methanol followed by 2M ammonia/methanol. The appropriate fractions were combined and evaporated in vacuo to give crude product (2.1 g) which was dissolved in DCM and purified on silica (100 g) using a 0-50% ethyl acetate-cyclohexane gradient over 60 min. The appropriate fractions were combined and evaporated in vacuo to give a sticky yellow solid which was triturated with petroleum ether (40-60), collected by filtration and dried in vacuo to give the title compound (500 mg).

LCMS (System A): $t_{RET}$=0.79 min; MH$^+$ 227

Intermediate 32: Methyl 5-({[(methyloxy)methyl]oxy}methyl)imidazo[1,2-a]pyridine-8-carboxylate To a stirred suspension of methyl 2-amino-6-({[(methyloxy)methyl]oxy}methyl)-3-pyridinecarboxylate (496 mg, 2.192 mmol) and sodium bicarbonate (193 mg, 2.302 mmol) in a mixture of methanol (15 mL) and water (7.5 mL) was added chloroacetaldehyde (50% wt. solution in water, 0.311 mL, 2.412 mmol). The mixture was heated to reflux for 2 hours when LCMS indicated that no reaction has occurred. More chloroacetaldehyde (0.311 mL, 2.412 mmol) was added and heating continued for 16 hours when LCMS indicated the reaction to be complete. The mixture was partitioned between ethyl acetate (50 mL) and saturated aqueous sodium bicarbonate (50 mL). The organic phase was separated and the aqueous phase back extracted with ethyl acetate (50 mL). The combined organic extracts were dried ($MgSO_4$), filtered and concentrated in vacuo to give crude product (450 mg). This material was dissolved in DCM and purified on silica (50 g) using a 0-25% methanol-DCM gradient over 60 min. The appropriate fractions were combined and evaporated in vacuo to give the title compound as an orange oil (386 mg).

LCMS (System A): $t_{RET}$=0.68 min; MH$^+$ 251

Intermediate 33: N-{trans-3-[(2,3-Dichlorophenyl)oxy]cyclobutyl}-5-({[(methyloxy)methyl]oxy}methyl)imidazo[1,2-a]pyridine-8-carboxamide A suspension of methyl 5-({[(methyloxy)methyl]oxy}methyl)imidazo[1,2-a]pyridine-8-carboxylate (438 mg, 1.75 mmol), trans-3-[(2,3-dichlorophenyl)oxy]cyclobutanamine (463 mg, 1.995 mmol) and triazabicyclodecene (75 mg, 0.539 mmol) in THF (0.5 mL) was stirred in a sealed tube at room temperature for 18 hours. The reaction mixture was then transferred to a round bottomed flask using DCM as solvent and evaporated in vacuo to give yellow/brown gum which solidified (1.5 g). This material was dissolved in DCM and purified on silica (70 g) using a 0-100% ethyl acetate-cyclohexane gradient over 40 min. The appropriate fractions were combined and evaporated in vacuo to give the title compound as yellow crystals (601 mg).

LCMS (System A): $t_{RET}$=1.05 min; MH$^+$ 450, 452, 454

Intermediate 34: N-{trans-3-[(2,3-Dichlorophenyl)oxy]cyclobutyl}-5-(hydroxymethyl)imidazo[1,2-a]pyridine-8-carboxamide To a stirred suspension of N-{trans-3-[(2,3-dichlorophenyl)oxy]cyclobutyl}-5-({[(methyloxy)methyl]oxy}methyl)imidazo[1,2-a]pyridine-8-carboxamide (598 mg, 1.328 mmol) in THF (5 mL) was added 5 to 6M HCl in 2-propanol (5 mL, 27.5 mmol) and a clear solution was observed. The reaction mixture was stirred under a nitrogen atmosphere at room temperature for 1 hour. More 5-6M HCl in 2-propanol (0.5 mL) was added and stirring continued for another hour when HPLC indicated the reaction to be complete. The mixture was concentrated in vacuo to give a colourless gum (2.163 g). This material was partitioned between ethyl acetate (30 mL) and sodium bicarbonate (2×15 mL). The organic phase was separated, washed with brine (15 mL), dried over magnesium sulphate and evaporated in vacuo to give the title compound as a yellow solid (537 mg).

LCMS (System A): $t_{RET}$=0.88 min; MH$^+$ 405, 407, 409

PREPARATION OF EXAMPLES

Example 1 trans-N-(Imidazo[1,2-a]pyridin-8-ylmethyl)-3-{[3-(trifluoromethyl)phenyl]oxy}cyclobutanamine

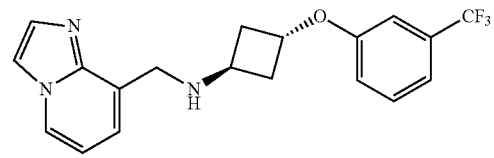 [SMILES: FC(F)(F)c1cccc(O[C@H]2C[C@H](NCc3cccn4ccnc34)C2)c1]

1,1-Dimethylethyl(imidazo[1,2-a]pyridin-8-ylmethyl)(trans-3-{[3-(trifluoromethyl)phenyl]oxy}cyclobutyl)carbamate (48.2 mg, 0.104 mmol) was stirred in 4M HCl in dioxane (5 mL, 20 mmol) for 3 hours when LCMS indicated the reaction to be complete. The mixture was loaded onto a SCX cartridge (2 g) and eluted with MeOH (3 column volumes) and flushed with ammonia in MeOH. The eluant was concentrated in vacuo to give the title compound (37 mg).

LCMS (System B): $t_{RET}$=2.81 min; MH$^+$ 362

Example 2 trans-3-[(2,3-Dichlorophenl)oxy]-N-(imidazo[1,2-a]pyridin-8-ylmethyl)cyclobutanamine

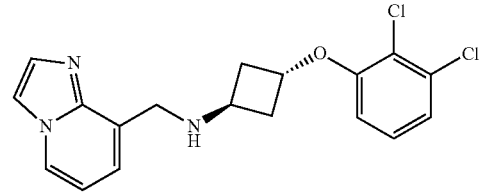 [SMILES: Clc1cccc(O[C@H]2C[C@H](NCc3cccn4ccnc34)C2)c1Cl]

To a stirred solution of 1,1-dimethylethyl {trans-3-[(2,3-dichlorophenyl)oxy]cyclobutyl}(imidazo[1,2-a]pyridin-8-ylmethyl)carbamate (55 mg, 0.119 mmol) in DCM (0.5 mL) was added neat TFA (0.5 mL, 6.49 mmol). The reaction was stirred at ambient temperature for 16 hours when LCMS indicated the reaction to be complete. The reaction was concentrated using a blowdown unit and the residue was dissolved in 1:1 MeOH:DMSO (1 mL) and purified by MDAP. Product containing fractions were dried under a stream of nitrogen to give the title compound as a brown gum (25 mg).

LCMS (System B): $t_{RET}$=2.84 min; MH$^+$ 362, 364, 366

Example 2A trans-3-[(2,3-Dichlorophenyl)oxy]-N-(imidazo[1,2-a]pyridin-8-ylmethyl)cyclobutanamine, maleate salt

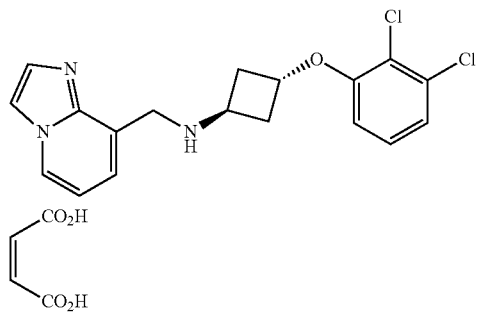

Maleic acid (30.4 mg, 0.262 mmol) was added to a solution of trans-3-[(2,3-dichlorophenyl)oxy]-N-(imidazo[1,2-a]pyridaoapyrdin-8-ylmethyl)cyclobutanamine (95 mg, 0.262 mmol) in methanol (2 mL) and the sample left to stand at room temperature for 15 min and then evaporated to dryness in a nitrogen blow-down unit at 45° C. Diethyl ether was added to the residue and the sticky residue was worked with a spatula to give a suspension which was evaporated to dryness in a nitrogen blow-down unit at 45° C. to give the title compound as a cream solid (92 mg).

LCMS (System B): $t_{RET}$=2.84 min; MH$^+$ 362, 364, 366

Example 3 cis-3-[(23-dichlorophenyl)oxy]-N-(imidazo[1,2-a]pyridin-8-ylmethyl)cyclobutanamine

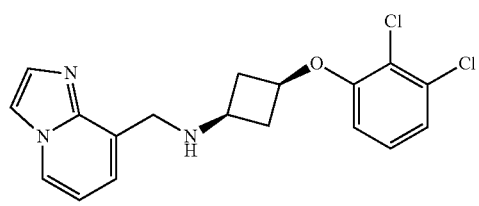 [SMILES: Clc1cccc(O[C@H]2C[C@@H](NCc3cccn4ccnc34)C2)c1Cl]

A suspension of cis-3-[(2,3-dichlorophenyl)oxy]cyclobutanamine hydrochloride salt (184 mg, 0.684 mmol) in anhydrous DCM (5 mL) was treated with DIPEA (0.143 mL, 821 mmol). A solution of imidazo[1,2-a]pyridine-8-carbaldehyde (100 mg, 0.684 mmol) in anhydrous DCM (5 mL) was added and the reaction was stirred at room temperature for 2 hours. Sodium triacetoxyborohydride (290 mg, 1.368 mmol) was added portionwise and the reaction was stirred at room temperature under nitrogen for 17 hours when LCMS showed formation of the desired product. Water (20 mL) was added and the organic layer was separated, passed through a hydrophobic frit and concentrated under reduced pressure. The residue was dissolved in 1:1 DMSO/MeOH (3 mL) and purified by reverse phase MDAP (Method B, 3 injections). Product containing fractions were dried to give the title compound as a brown gum (166.6 mg).

LCMS (System B): $t_{RET}$=2.76 min; MH$^+$ 362, 364, 366

Example 4 trans-3-{[2-Chloro-3-(trifluoromethyl)phenyl]oxy}-N-(imidazo[1,2-a]pyridin-8-ylmethyl)cyclobutanamine

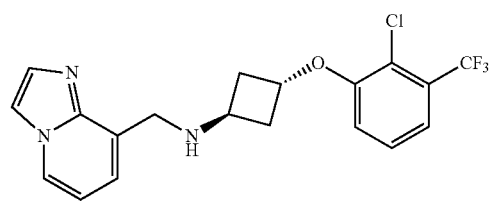 [SMILES: FC(F)(F)c1cccc(O[C@H]2C[C@H](NCc3cccn4ccnc34)C2)c1Cl]

Prepared similarly to Example 1 from 1,1-dimethylethyl (trans-3-{[2-chloro-3-(trifluoromethyl)phenyl]oxy}cyclobutyl)(imidazo[1,2-a]pyridin-8-ylmethyl)carbamate.

LCMS (System B): $t_{RET}$=2.92 min; MH$^+$ 396, 398

Example 5 trans-3-[(3-Chloro-4-fluorophenyl)oxy]-N-(imidazo[1,2-a]pyridin-8-ylmethyl)cyclobutanamine, trifluoroacetate

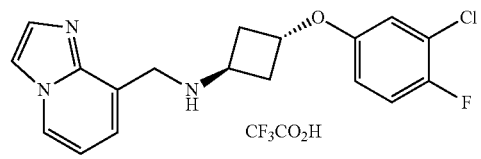 [SMILES: Fc1ccc(O[C@H]2C[C@H](NCc3cccn4ccnc34)C2)cc1Cl ; "CF3CO2H"]

1,1-Dimethylethyl(cis-3-hydroxycyclobutyl)(imidazo[1,2-a]pyridin-8-ylmethyl)carbamate (0.032 g, 0.1 mmol), 3-chloro-4-fluorophenol (22 mg, 0.15 mmol) and triphenylphosphine (0.039 g, 0.15 mmol) were combined in THF (0.6 mL). Diisopropyl azodicarboxylate (0.029 mL, 0.15 mmol) was then added and the solution stirred at 75° C. for 18 hours. More 3-chloro-4-fluorophenol (0.15 mmol), triphenylphosphine (1.5 mmol) and diisopropyl azodicarboxylate (1.5 mmol) were added and the solution heated at 75° C. for a further 6 hours when LCMS indicated reaction occurring and the mixture was kept at 75° C. overnight and then the solvent was removed using a blowdown unit. The residue was dissolved in DMSO (1 mL) and purified by MDAP to give the BOC protected intermediate which was directly deprotected by dissolving in TFA (0.2 mL) and DCM (0.2 mL) and stirring at room temperature for 3 hours. Evaporation using a blowdown unit gave the title compound (6.1 mg).

LCMS (System A): $t_{RET}$=0.63 min; MH$^+$ 346, 348

Example 6 trans-3-{[4-Chloro-3-(trifluoromethyl)phenyl]oxy}-N-(imidazo[1,2-a]pyridin-8-ylmethyl)cyclobutanamine

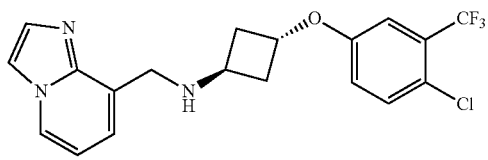 [SMILES: FC(F)(F)c1cc(O[C@H]2C[C@H](NCc3cccn4ccnc34)C2)ccc1Cl]

Prepared similarly to Example 1 from 1,1-dimethylethyl (trans-3-{[4-chloro-3-(trifluoromethyl)phenyl]oxy}cyclobutyl)(imidazo[1,2-a]pyridin-8-ylmethyl)carbamate with additional purification by MDAP.
LCMS (System B): $t_{RET}$=2.92 min; $MH^+$ 396, 398

Example 7 trans-3-{[4-Fluoro-3-(trifluoromethyl)phenyl]oxy}-N-(imidazo[1,2-a]pyridin-8-ylmethyl)cyclobutanamine

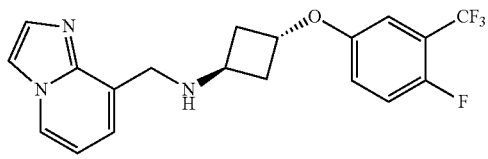 [SMILES: Fc1ccc(O[C@H]2C[C@H](NCc3cccn4ccnc34)C2)cc1C(F)(F)F]

1,1-Dimethylethyl(trans-3-{[4-fluoro-3-(trifluoromethyl)phenyl]oxy}cyclobutyl)(imidazo[1,2-a]pyridin-8-ylmethyl)carbamate (62 mg, 0.129 mmol) was stirred in 4M HCl in dioxane (5 mL, 20 mmol) for 3 hours when LCMS indicated the reaction to be complete. The mixture was loaded onto a SCX cartridge (2 g) and eluted with MeOH (3 column volumes) and flushed with ammonia in MeOH. The eluant was concentrated in vacuo to give slightly impure product which was dissolved in 50:50 DMSO/MeOH (1 mL) and purified by MDAP to give the title compound (16.8 mg).
LCMS (System B): $t_{RET}$=2.85 min; $MH^+$ 380
$^1$H NMR (400 MHz, Methanol-$d_4$) δ ppm 2.26-2.40 (m, 4H) 3.54-3.63 (m, 1H) 4.04 (s, 2H) 6.89 (t, J=6.78 Hz, 1H) 6.98-7.07 (m, 1H) 7.16-7.24 (m, 1H) 7.27 (d, J=6.78 Hz, 1H) 7.57 (d, J=1.25 Hz, 1H) 7.85 (d, J=1.25 Hz, 1H) 8.36 (d, J=6.78 Hz, 1H).

Example 7A trans-3-{[4-Fluoro-3-(trifluoromethyl)phenyl]oxy}-N-(imidazo[1,2-a]pyridin-8-ylmethyl)cyclobutanamine, hydrochloride salt

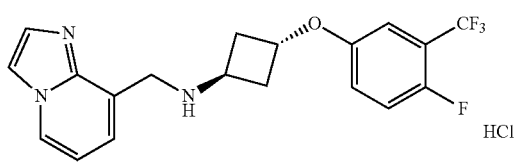 [SMILES: Fc1ccc(O[C@H]2C[C@H](NCc3cccn4ccnc34)C2)cc1C(F)(F)F ; Cl]

A stirred suspension of trans-3-{[4-fluoro-3-(trifluoromethyl)phenyl]oxy}cyclobutanamine hydrochloride (6.19 g, 21.67 mmol) in anhydrous DCM (60 mL), under nitrogen, was treated with DIPEA (4.54 mL, 26.0 mmol) resulting in a colourless solution. A solution of imidazo[1,2-a]pyridine-8-carbaldehyde (3.17 g, 21.67 mmol) in anhydrous DCM (50 mL) was added and stirring was continued for 1 h. Sodium triacetoxyborohydride (9.18 g, 43.3 mmol) was added portionwise over 15 mins. The reaction mixture was stirred at ambient temperature for 3 h and then quenched slowly with saturated sodium bicarbonate (100 mL). The layers were separated and the aqueous phase was further extracted with DCM (50 mL). The combined organic extracts were washed successively with water (100 mL) and brine (50 mL), dried ($Na_2SO_4$) then evaporated in vacuo to give an orange oil (8.34 g). HPLC showed the intended product plus minor impurities. This material was dissolved in ether (75 mL) and treated with 2M HCl in ether (21.67 mL, 43.3 mmol) to give a precipitate which was filtered under reduced pressure and washed with ether. The solid appeared hygroscopic so it was swiftly transferred to a vacuum oven at 40° C. to yield a cream-coloured solid (9.60 g). HPLC showed this material to be 90.8% pure and it was treated with acetonitrile (120 mL) and heated to reflux. The solid failed to dissolve and so the mixture was allowed to cool to ambient temp, filtered under reduced pressure, washed with cold acetonitrile and dried in a vacuum oven at 40° C. to yield a white solid (7.91 g, 95% pure by HPLC). This material was combined a second batch of material of similar purity (4.9 g) and slurried in isopropanol (250 mL) and heated to a gentle reflux. Additional isopropanol was added until complete dissolution was achieved (total volume of isopropanol 400 mL). The mixture was allowed to cool to ambient temperature with slow overhead stirring (whilst the solution was still fairly hot it was seeded with a crystal from an earlier preparation). As the mixture cooled a mass of very fine white needles crystallised and after stirring for ca. 4 h at ambient temp the mixture was filtered under reduced pressure. The solid was washed with cold isopropanol (ca. 20 mL) and dried in a vacuum oven at 50° C. overnight to give the title compound as white crystals (10.13 g).
LCMS (System A): $t_{RET}$=0.67 min; $MH^+$ 380

Example 7B trans-3-{[4-Fluoro-3-(trifluoromethyl)phenyl]oxy}-N-(imidazo[1,2-a]pyridin-8-ylmethyl)cyclobutanamine, maleate salt

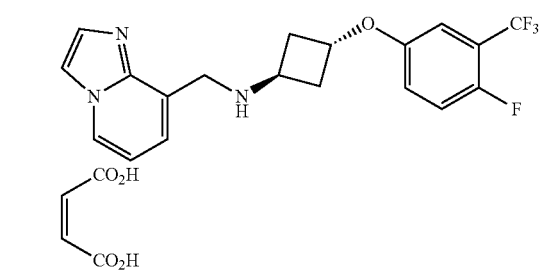

trans-3-{[4-Fluoro-3-(trifluoromethyl)phenyl]oxy}-N-(imidazo[1,2-a]pyridin-8-ylmethyl)cyclobutanamine (1035 mg, 2.73 mmol) and maleic acid (317 mg, 2.73 mmol) were dissolved in methanol (20 mL) and the solution stirred for 30 minutes. It was then concentrated in vacuo to give an orange gum. Diethyl ether was added to this residue to precipitate out the salt as a solid. The ether was removed in vacuo to give the title compound as a pale orange solid (1.299 g, 2.62 mmol).
LCMS (System A): $t_{RET}$=0.67 min; $MH^+$ 380

Example 8 trans-3-{[2-Chloro-4-(trifluoromethyl)phenyl]oxy}-
N-(imidazo[1,2-a]pyridin-8-ylmethyl)cyclobutan-
amine

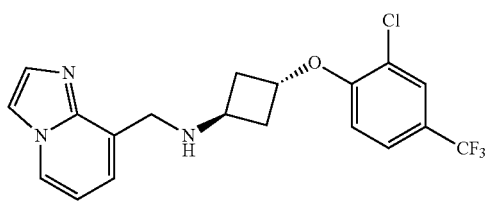 [SMILES: FC(F)(F)c1ccc(O[C@H]2C[C@H](NCc3cccn4ccnc34)C2)c(Cl)c1]

Prepared similarly to Example 1 from 1,1-dimethylethyl (trans-3-{[2-chloro-4-(trifluoromethyl)phenyl]oxy}cyclobutyl)(imidazo[1,2-a]pyridin-8-ylmethyl)carbamate with additional purification by MDAP.
LCMS (System B): $t_{RET}$=3.02 min; MH$^+$ 396, 398

Example 9 trans-3-{[4-Chloro-2-(trifluoromethyl)phenyl]oxy}-
N-(imidazo[1,2-a]pyridin-8-ylmethyl)cyclobutan-
amine

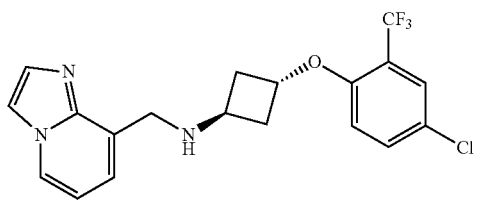 [SMILES: FC(F)(F)c1cc(Cl)ccc1O[C@H]1C[C@H](NCc2cccn3ccnc23)C1]

Prepared similarly to Example 1 from 1,1-dimethylethyl (trans-3-{[4-chloro-2-(trifluoromethyl)phenyl]oxy}cyclobutyl)(imidazo[1,2-a]pyridin-8-ylmethyl)carbamate.
LCMS (System B): $t_{RET}$=3.03 min; MH$^+$ 396, 398

Example 10 trans-3-{[3-Chloro-5-(trifluoromethyl)phenyl]oxy}-
N-(imidazo[1,2-a]pyridin-8-ylmethyl)cyclobutan-
amine

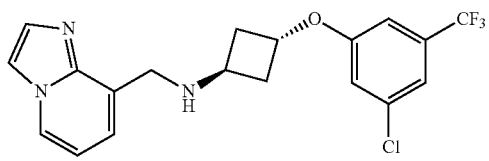 [SMILES: FC(F)(F)c1cc(Cl)cc(O[C@H]2C[C@H](NCc3cccn4ccnc34)C2)c1]

Prepared similarly to Example 1 from 1,1-dimethylethyl (trans-3-{[3-chloro-5-(trifluoromethyl)phenyl]oxy}cyclobutyl)(imidazo[1,2-a]pyridin-8-ylmethyl)carbamate but with two additional sequential purifications by MDAP.
LCMS (System B): $t_{RET}$=3.11 min; MH$^+$ 396, 398

Example 11 trans-3-{[4-(1,1-Dimethylethyl)-3,5-difluorophenyl]
oxy}-N-(imidazo[1,2-a]pyridin-8-ylmethyl)cyclobu-
tanamine

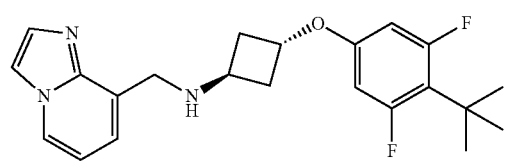 [SMILES: CC(C)(C)c1c(F)cc(O[C@H]2C[C@H](NCc3cccn4ccnc34)C2)cc1F]

A suspension of trans-3-{[4-(1,1-dimethylethyl)-3,5-difluorophenyl]oxy}cyclobutanamine (73 mg, 0.286 mmol) in anhydrous DCM (3 mL) was treated with DIPEA (0.06 mL, 0.343 mmol). A solution of imidazo[1,2-a]pyridine-8-carbaldehyde (41.8 mg, 0.286 mmol) in anhydrous DCM (3 mL) was added and the reaction was stirred at room temperature for 15 min. Sodium triacetoxyborohydride (121 mg, 0.572 mmol) was added portionwise and the reaction was stirred at room temperature under nitrogen overnight. Water (10 mL) was added and the phases were separated. The organic layer was concentrated and the residue was purified by MDAP to give the title compound (79.4 mg).
LCMS (System B): $t_{RET}$=3.39 min; MH$^+$ 386

Example 12 cis-3-{[4-(1,1-Dimethylethyl)-3,5-difluorophenyl]
oxy}-N-(imidazo[1,2-a]pyridin-8-ylmethyl)cyclobu-
tanamine

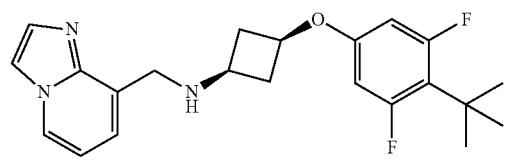 [SMILES: CC(C)(C)c1c(F)cc(O[C@H]2C[C@@H](NCc3cccn4ccnc34)C2)cc1F]

Prepared similarly to Example 1 from imidazo[1,2-a]pyridine-8-carbaldehyde and cis-3-{[4-(1,1-dimethylethyl)-3,5-difluorophenyl]oxy}cyclobutanamine hydrochloride. LCMS (System B): $t_{RET}$=3.28 min; MH$^+$ 386

Example 13

{8-[({trans-3-[(2,3-Dichlorophenyl)oxy]
cyclobutyl}amino)methyl]imidazo[1,2-a]pyridin-5-
yl}methanol

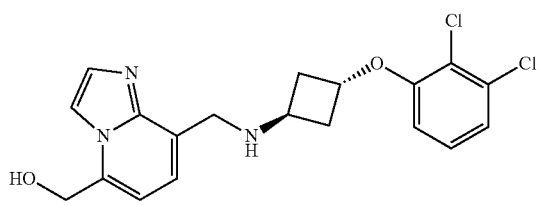 [SMILES: OCc1ccc(CN[C@H]2C[C@H](Oc3cccc(Cl)c3Cl)C2)c2nccn12]

Method A

To a stirred solution of trans-3-[(2,3-dichlorophenyl)oxy]-N-{[5-({[(methyloxy)methyl]oxy}methyl)imidazo[1,2-a]pyridin-8-yl]methyl}cyclobutanamine (26 mg, 0.06 mmol) in DCM (1 mL) was added neat TFA (1 mL, 12.98 mmol) and the reaction warmed to 50° C. for 2 hours when LCMS indicated the reaction to be complete. The reaction was concentrated in vacuo and the residue was dissolved in 1:1 MeOH:DMSO (1 mL) and purified by MDAP. Product containing fractions were combined and dried under a stream of nitrogen to give the title compound (10 mg).

LCMS (System C): $t_{RET}$=1.04 min; MH$^+$ 392, 394, 396

Method B

To degassed THF (5 mL) was added 2M lithium borohydride in THF (2.64 mL, 5.28 mmol) under nitrogen at room temperature. Trimethylchloride silane (1.340 mL, 10.55 mmol) was added and the reaction mixture was stirred at room temperature for 15 min. This solution was then added to a degassed solution of N-{trans-3-[(2,3-dichlorophenyl)oxy]cyclobutyl}-5-(hydroxymethyl)imidazo[1,2-a]pyridine-8-carboxamide (536 mg, 1.319 mmol) and trimethylchloride silane (0.251 mL, 1.979 mmol) in THF (10 mL) and the mixture stirred for 120 hours. The reaction mixture was then cooled to 0° C. and quenched with 2M HCl (10 ml) and methanol (10 mL). The reaction was exothermic and effervescence was observed. The reaction mixture was allowed to warm to room temperature and stirred for 3 hours and was then concentrated in vacuo. The residue was partitioned between ethyl acetate and sodium bicarbonate which gave an emulsion. Brine was added and the organic phase was separated, dried over magnesium sulphate, filtered through a hydrophobic frit and then evaporated in vacuo to give an off-white solid (608 mg). This material was dissolved in 1:1 MeOH/DMSO and purified on reverse phase silica (C18, 120 g) using a 5-35% acetonitrile (+0.1% TFA)-water (+0.1% TFA) gradient over 22 column volumes. The appropriate fractions were combined and the solvent was concentrated in vacuo to give an aqueous solution of crude product which was treated with sodium bicarbonate (solid) until a white precipitate was observed. The suspension was extracted with ethyl acetate (3×100 mL). The combined organic extracts were washed with brine and dried over magnesium sulphate and concentrated in vacuo to leave a white foamy solid (135 mg). This material was dissolved in 1:1 MeOH:DMSO (2×1 mL) and purified by MDAP on a Sunfire C18 column using acetonitrile-water with a formic acid modifier as eluant. The product containing fractions were evaporated and the residue (58 mg) was combined with similar material (14 mg) from a similar reaction and partitioned between DCM (20 mL) and sodium bicarbonate (20 mL). The aqueous phase was extracted again with DCM (2×20 mL) and the combined the organic extracts were washed with brine, dried over magnesium sulphate and evaporated in vacuo to give a pale yellow foam (60 mg). This material was only 92% pure and was subjected once more to MDAP purification on a Sunfire C18 column using acetonitrile-water with a formic acid modifier as eluant. The product containing fractions were concentrated in vacuo and the solution treated with sodium bicarbonate until alkaline, to give a cloudy solution. This suspension was extracted with ethyl acetate (20 mL) and the extract was washed with brine (10 mL), dried over magnesium sulphate and concentrated in vacuo to give the title compound as a white solid (42 mg).

LCMS (System C): $t_{RET}$=1.08 min; MH$^+$392, 394, 396

Example 14

(8-{[(trans-3-{[4-Fluoro-3-(trifluoromethyl)phenyl]oxy}cyclobutyl)amino]methyl}imidazo[1,2-a]pyridin-5-yl)methanol

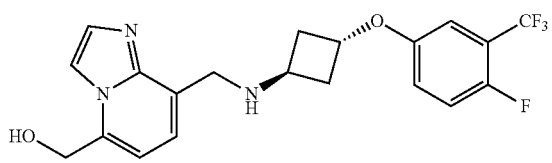 [SMILES: OCc1ccc(CN[C@H]2C[C@H](Oc3ccc(F)c(C(F)(F)F)c3)C2)c2nccn12]

Prepared similarly to Example 13 from trans-3-{[4-fluoro-3-(trifluoromethyl)phenyl]oxy}-N-{[5-({[(methyloxy)methyl]oxy}methyl)imidazo[1,2-a]pyridin-8-yl]methyl}cyclobutanamine.

LCMS (System C): $t_{RET}$=1.04 min; MH$^+$ 410

Example 15

{8-[({trans-3-[(2,3-Dichlorophenyl)oxy]cyclobutyl}amino)methyl]imidazo[1,2-a]pyridin-3-yl}methanol

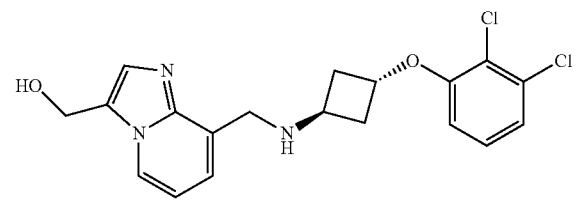 [SMILES: OCc1cnc2c(CN[C@H]3C[C@H](Oc4cccc(Cl)c4Cl)C3)cccn12]

To a solution of ethyl 3-({[(1,1-dimethylethyl)(dimethyl)silyl]oxy}methyl)imidazo[1,2-a]pyridine-8-carboxylate (300 mg, 0.897 mmol) in THF (5 mL) at −78° C. under nitrogen was added dropwise, over 10 minutes, diisobutylaluminium hydride (1M in hexanes, 0.9 mL, 0.9 mmol) and the reaction mixture stirred at −78° C. for a further 2.5 hours. The reaction was then allowed to warm slowly to room temperature and stirred under nitrogen for a further 16.5 hours when LCMS indicated the reaction to be incomplete. The reaction was cooled again to −78° C. and more diisobutylaluminium hydride (1M in hexanes, 0.9 mL, 0.9 mmol) was added and stirring continued at −78° C. under nitrogen for a further 2.5 hours when LCMS indicated complete reaction. The mixture was quenched with water (10 mL) and extracted with DCM (50 mL). The organic layer was separated and washed sequentially with saturated aqueous ammonium chloride solution (50 mL) and brine (50 mL) and then dried using a hydrophobic frit and evaporated in vacuo. The residue was dissolved in DCM and purified on a silica cartridge (50 g) using a 0-25% methanol-dichloromethane gradient over 40 mins. Product containing fractions were combined and evaporated to give impure 3-({[(1,1-dimethylethyl)(dimethyl)silyl]oxy}methyl)imidazo[1,2-a]pyridine-8-carbaldehyde as a yellow oil. To a solution of this impure aldehyde (121 mg, 0.417 mmol) in MeOH (3 mL) and DCM (1 mL) was added magnesium sulphate (250 mg, 2.077 mmol), trans-3-[(2,3-dichlorophenyl)oxy]cyclobutanamine hydrochloride (120 mg, 0.447 mmol) and DIPEA (0.08 mL, 0.458 mmol) and the reaction mixture stirred at room temperature for 15 mins under nitrogen. Sodium triacetoxyborohydride (350 mg, 1.651 mmol) was then added and the reaction mixture was stirred under nitrogen for a further 22 hours when LCMS showed the reaction to be incomplete. More sodium triacetoxyborohydride (350 mg, 1.651 mmol) was then added and the mixture stirred under nitrogen at room temperature for 3 hours when LCMS indicated complete reaction. Saturated aqueous sodium bicarbonate solution (10 mL) was then added followed by DCM (15 mL). The organic layer was separated and dried through a hydrophobic frit and the solvent evaporated in vacuo. The residue was dissolved in DCM and purified on a silica cartridge (10 g) using a 0-25% methanol-DCM gradient over 40 mins. The appropriate fractions were combined and evaporated in vacuo to give to give the crude TBDMS protected product. This material was dissolved in THF (10 mL) and tetrabutylammonium fluoride in THF (1M, 0.46 mL, 0.46 mmol) was added and the reaction mixture stirred at room temperature under nitrogen for 18 hours. The reaction mixture was concentrated in vacuo and the residue was dissolved in DCM and purified on a silica cartridge (20 g) using a 0-25% methanol-dichloromethane gradient over 40 min. The product containing fractions were combined and evaporated in vacuo to give still impure material (ca. 200 mg) which was dissolved in 1:1 MeOH:DMSO (2×1 mL) and re-purified by MDAP. Product containing fractions were dried under a stream of nitrogen to give the title compound (16 mg).

LCMS (System C): $t_{RET}$=1.06 min; MH$^+$ 392, 394, 396

Example 16 cis-3-{[2-Chloro-3-(trifluoromethyl)phenyl]oxy}-N-(imidazo[1,2-a]pyridin-8-ylmethyl)cyclobutanamine, maleate salt

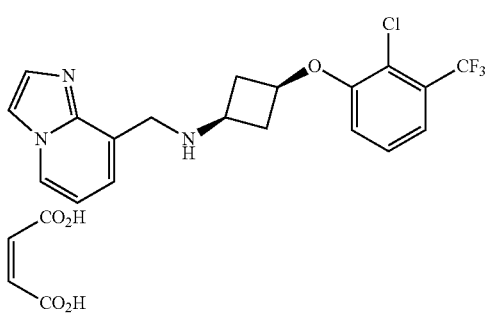

1,1-Dimethylethyl(cis-3-{[2-chloro-3-(trifluoromethyl)phenyl]oxy}cyclobutyl)(imidazo[1,2-a]pyridin-8-ylmethyl) carbamate (233 mg, 0.47 mmol) was stirred in 4M HCl in dioxane (5 mL, 20 mmol) for 3 hours when LCMS indicated the reaction to be complete. The mixture was loaded onto a SCX cartridge (5 g) and eluted with MeOH (3 column volumes) and flushed with ammonia in MeOH. The eluant was concentrated in vacuo to give the product as the free base (91 mg). This material was dissolved in methanol (2 mL) and maleic acid (26.7 mg, 0.23 mmol) was added and the mixture left to stand at room temperature for 15 min. The sample was evaporated to dryness in a nitrogen blow-down unit at 45° C. and diethyl ether was added. Scratching the sticky residue with a spatula gave a suspension which was evaporated to dryness in the nitrogen blow-down unit at 45° C. to give the title compound as a yellow solid (120.4 mg).

LCMS (System B): $t_{RET}$=2.85 min; MH$^+$ 396, 398

Example 17 cis-3-{[4-Fluoro-3-(trifluoromethyl)phenyl]oxy}-N-(imidazo[1,2-a]pyridin-8-ylmethyl)cyclobutanamine, maleate salt

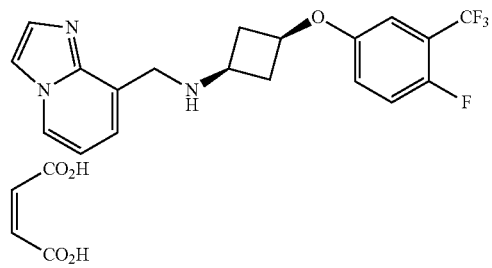

Prepared similarly to Example 16 by acidic deprotection of 1,1-dimethylethyl (cis-3-{[4-fluoro-3-(trifluoromethyl)phenyl]oxy}cyclobutyl)(imidazo[1,2-a]pyridin-8-ylmethyl)carbamate followed by conversion of the product into the maleate salt with maleic acid.

LCMS (System B): $t_{RET}$=2.78 min; MH$^+$ 380

X-Ray Powder Diffraction (XRPD)

Example 7A

XRPD data for Example 7A were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Characteristic XRPD angles and d-spacings are recorded in Table 1. The margin of error is approximately ±0.1° 2θ for each of the peak assignments. Peak intensities may vary from sample to sample due to preferred orientation. Peak positions were measured using Highscore software.

TABLE 1

Characteristic XRPD peak positions and d-spacings for Example 7A: trans-3-{[4-Fluoro-3-(trifluoromethyl)phenyl]oxy}-N-(imidazo[1,2-a]pyridin-8-ylmethyl)cyclobutanamine, hydrochloride salt

| 2θ/° | d-spacings/Å |
| --- | --- |
| 5.7 | 15.6 |
| 8.7 | 10.2 |
| 11.3 | 7.8 |
| 12.7 | 7.0 |
| 14.4 | 6.1 |
| 14.9 | 5.9 |
| 17.0 | 5.2 |
| 19.2 | 4.6 |
| 21.8 | 4.1 |
| 23.1 | 3.9 |
| 24.1 | 3.7 |

TABLE 1-continued

Characteristic XRPD peak positions and d-spacings for Example 7A:
trans-3-{[4-Fluoro-3-(trifluoromethyl)phenyl]oxy}-N-(imidazo[1,2-a]pyridin-8-ylmethyl)cyclobutanamine, hydrochloride salt

| 2θ/° | d-spacings/Å |
|---|---|
| 24.8 | 3.6 |
| 25.6 | 3.5 |

A representative XRPD diffractogram of Example 7A is shown in FIG. 1.

Example 7B

XRPD data for Example 7B were acquired on a Rigaku Miniflex II, powder diffractometer. The acquisition conditions were: radiation: Cu Kα, generator tension: 30 kV, generator current: 15 mA, start angle: 2.0° 2θ, end angle: 40.0° 2θ, step size: 0.020° 2θ. The time per step was 1 s. The sample was prepared by mounting a few milligrams of sample on a Si wafer (zero background) plate, resulting in a thin layer of powder.

Characteristic XRPD angles and calculated d-spacings are recorded in Table 2. The experimental error in the peak positions is approximately ±0.1° 2θ. These were calculated from the raw data using Jade software

TABLE 2

Characteristic XRPD peak positions and d-spacings for Example 7B:
trans-3-{[4-Fluoro-3-(trifluoromethyl)phenyl]oxy}-N-(imidazo[1,2-a]pyridin-8-ylmethyl)cyclobutanamine, maleate salt.
A representative XRPD diffractogram of Example 7B is shown in FIG. 2.

| 2θ/° | d-spacings/Å |
|---|---|
| 8.456 | 10.4 |
| 12.402 | 7.1 |
| 13.402 | 6.6 |
| 15.262 | 5.8 |
| 16.001 | 5.5 |
| 16.934 | 5.2 |
| 18.322 | 4.8 |
| 19.199 | 4.6 |
| 19.96 | 4.4 |
| 20.48 | 4.3 |
| 21.159 | 4.2 |
| 22.122 | 4.0 |
| 22.662 | 3.9 |
| 23.278 | 3.8 |
| 24.301 | 3.7 |
| 24.96 | 3.6 |
| 25.5 | 3.5 |
| 26.141 | 3.4 |
| 27.02 | 3.3 |
| 27.757 | 3.2 |
| 28.202 | 3.2 |
| 28.699 | 3.1 |
| 29.28 | 3.0 |
| 29.745 | 3.0 |
| 30.947 | 2.9 |
| 31.423 | 2.8 |
| 31.742 | 2.8 |
| 32.461 | 2.8 |
| 32.801 | 2.7 |
| 33.64 | 2.7 |
| 34.14 | 2.6 |
| 34.902 | 2.6 |
| 36.656 | 2.4 |
| 37.28 | 2.4 |
| 37.747 | 2.4 |
| 39.202 | 2.3 |

Biological Assays

Assays for the functional inhibition of TRPV1 Ion Channel by test compound using Capsaicin or Acid Stimulus challenge were performed.

Compound Preparation

Compounds were dissolved in DMSO to 1 mM. An 11 point 4 fold serial dilution was prepared and 0.5 ul dispensed into Greiner black clear bottom 384 well plates.

Preparation of Recombinant HEK-293 Cells Expressing TRPV1 for Assay

HEK-293 cells stably expressing mitochondrial targeted Aequorin were transfected with TRPV1 receptor bacmam at scale for cryopreservation in 1 ml vial aliquots. Cells can be stored at −140° C. for up to 18 months.

18-20 hours before assay, cells were rapidly thawed in a water bath at 37° C. and transferred to a 50 ml Falcon tube. Cells were resuspended in 9 mls of M1 'generic' media (DMEM/F12 with 10% dialysed FBS-Invitrogen 041-95750V) for every 1 ml cells and then centrifuged for 5 min at 1000 rpm. The cell pellet was resuspended in ~10 mls loading buffer (Tyrodes Base Buffer*+0.1% Pluronic Acid F68 solution+0.1% BSA) and the pH was adjusted to 7.4 for Capsaicin stimulus assay or 6.7 for Acid stimulus assay. Cell density was calculated using the Trypan Blue stain method and adjusted to 2.5×10 e6 cells/ml using loading buffer. Coelentrazine (DiscoverX Cat. No 0-0084L-500 uM stock made in 100% ethanol) was added to a final concentration of 5 uM and the falcon tube was covered in foil (to protect from light) and placed on a windmill rotator at room temperature for approximately 20 hours.

*Base Buffer=Sigma kit T2145 was dissolved in deionised water, 20 mL HEPES solution (Sigma H0887) and 13.4 mL of NaHCO$_3$ (Sigma S8761) and made up to 1 L.

After loading, a cell count was taken and cell density adjusted accordingly depending on assay stimulus.

Capsaicin Assay for TRPV1 Receptor Antagonism

For Capsaicin stimulus assay cells were diluted to 1.25×10 e5 cells/ml using dilution buffer (Tyrodes Base Buffer+0.1% Pluronic Acid F68 solution) at pH 7.4

To the compound plates, the following additions were made:

20 ul dilution buffer at pH 7.4 followed by 20 ul cells were added to the test compound plate and any agonist activity measured as luminescence AUC counts. The compound/cell mix was incubated for 15 minutes and then challenged with 20 ul of a 4×EC$_{50}$ concentration of Capsaicin (calculated on the day of assay), with concomitant luminescence detection.

AUC data was exported from the reader and data analysis was performed using 4 parameter logistic model, with data normalised to nominal high and low controls within plate.

Each of Examples 1 to 17 had a pIC$_{50}$ of from 5.9 to 8.9 in the Capsaicin assay. Example 7A was not tested.

Each of Examples 1, 2, 2A, 4, 5, 6, 7, 7B, 8, 9, 11, 12, 13, 14, 15 had a pIC$_{50}$ of from 7.0 to 8.9 in the Capsaicin assay.

Acid Stimulus Assay for TRPV1 Receptor Antagonism

For Acid stimulus assay, cells were diluted to 2.5×10 e5 cells/ml using dilution buffer at pH 6.7.

The cells and the compound plates were added to the Lumilux™ reader (Perkin Elmer) with on-board liquid handling.

To the compound plates, the following additions were made:

20 ul dilution buffer at pH 6.7 followed by 20 ul cells were added to the test compound plate. The compound/cell mix was incubated for 15 minutes and then challenged with 20 ul of Acid Stimulus Buffer (NaCl 145 mM 8.48 g/L, KCl 2.5 mM 0.18 g/L, CaCl$_2$ 2 mM 0.294 g/L, MgCl$_2$ 1 mM 0.203 g/L, Glucose 10 mM 1.81 g/L, Sucrose 10 mM 8.76 g/L)+30 ul 1M HCL for every 10 ml Acid Stimulus Buffer (3 mM), with concomitant luminescence detection.

AUC data was exported from the reader and data analysis was performed using 4 parameter logistic model, with data normalised to nominal high and low controls within plate Each of Examples 1 to 17 had a $pIC_{50}$ of from 5.0 to 8.8 in this acid stimulus assay. Each of Examples 1, 2, 2A, 4, 5, 6, 7, 7B, 8, 9, 10, 11, 12, 13, 14 and 15 had a $pIC_{50}$ of from 5.7 to 8.8 in the acid stimulus assay. Example 7A was not tested.

Inhibition of i.v. Capsaicin Induced Bronchoconstriction in Anesthetized Guinea Pigs Male Hartley Guinea Pigs weighing between 400 and 700 g were anesthetized with ketamine/xylazine mixture (88/15 mg/kg, i.m.). Animals were placed on their back, a toe pinch was performed to ensure depth of anaesthesia and a section of skin and fur was dissected away from the neck. The trachea, jugular vein, and carotid artery were isolated and cannulated to allow for ventilation, drug delivery, and blood pressure monitoring. Compounds were delivered via intra-tracheal delivery (in 200 uL of 0.5% Tween 80) 1 hour before capsaicin challenge. Depth of anaesthesia was confirmed by toe pinch and the Guinea pigs were placed in the full body plethysmograph. The chamber was closed and the animal was paralyzed by administration of Gallamine (2 mg/kg i.v.). Animals were ventilated at ~1.0 mL/110 g, 60-65 breaths per minute by a Harvard Apparatus rodent respirator. Blood pressure and heart rate were continuously monitored to assess the level of anaesthesia, with supplemental anaesthetic doses given as required to maintain the proper level of anaesthesia. Capsaicin (20 ug/kg) was administered i.v. 1 hour after dosing of the compounds. The BioWindow Cardio Pulmonary Software version 1.02 (Modular Instruments, Inc.) recorded arterial pressure, pulmonary pressure and airflow. Air pressure delta (difference between maximum and minimum air pressure) was used as the primary readout of inhibition of the capsaicin induced bronchoconstriction. Animals were euthanized at the end of the experiment with an overdose of saturated KCl given i.v.

Results

In this model the compound of Example 7A was studied at dose of 0.005 (n=2), 0.025 (n=3), 0.05 (n=2), 0.1 (n=3), 0.5 (n=3) and 5 mg/kg (n=3) and a clear dose response for inhibition of capsaicin induced bronchoconstriction was observed from which an $ED_{50}$ of 33 ug/kg was estimated (FIG. 3—data for 0.025, 0.05, 0.1, and 0.5 mg/kg only shown for clarity).

In this model the compound of Example 13 was studied at a dose of 30 ug/kg (n=3) at which dose a 61% (+/−16.6%) inhibition of capsaicin induced bronchoconstriction was observed.

Solubility in Simulated Lung Fluid

The solubility of the compound of Example 7B in simulated lung fluid (Phosphate buffer, pH 6.9, 0.75 mM lecithin, 0.1% BSA) was measured at 37° C. over 4 hours as 1.779 mg/mL.

Preparation of an Aqueous Pharmaceutical Composition

The following illustrates the preparation of the aqueous pharmaceutical compositions and use thereof in accordance with this invention and is to be considered illustrating and not limiting the scope of the disclosure in any way.

The aqueous pharmaceutical compositions of the invention may be prepared according to the following general method.

The isotonicity adjusting agent(s) is charged into a suitable mixing vessel containing purified water and dissolved with stirring. Preservative(s) is pre-dissolved in purified water in a separate vessel, optionally with heating, for example to 50-60° C. depending on the preservative chosen, to aid dissolution, and then added to the isotonicity adjusting agent(s) with continuous stirring. The suspending agent(s) is then charged into the mixing vessel and dispersed throughout the solution. The resulting suspending vehicle is allowed to hydrate for an appropriate period of time to ensure crosslinkage and gelation, which may take 60 minutes or longer.

In a separate mixing vessel, the wetting agent(s) is mixed with purified water which optionally may be heated, for example to about 50-60° C. as appropriate depending on the wetting agent(s) chosen, and stirred to dissolve. A slurry of the compound or a pharmaceutically acceptable salt thereof (alone or in combination with a further active ingredient) is then prepared by adding the resultant wetting agent(s) solution to the active compound(s), which may be particle size reduced for example micronised, and mixed prior to homogenising/refining. Additionally, in a separate mixing vessel, additional preservative(s), if needed, may be diluted with purified water and stirred to mix.

Following the dispersion and gelation the slurry of active compound(s) is added to the mixing vessel containing the suspending agent and dispersed with stirring. Following the addition of the slurry of active compound(s), any additional preservative may be added to the bulk suspension and dispersed with continuous stirring. Finally, the suspension is made to its final mass by adding water and stirred.

Figure 1:
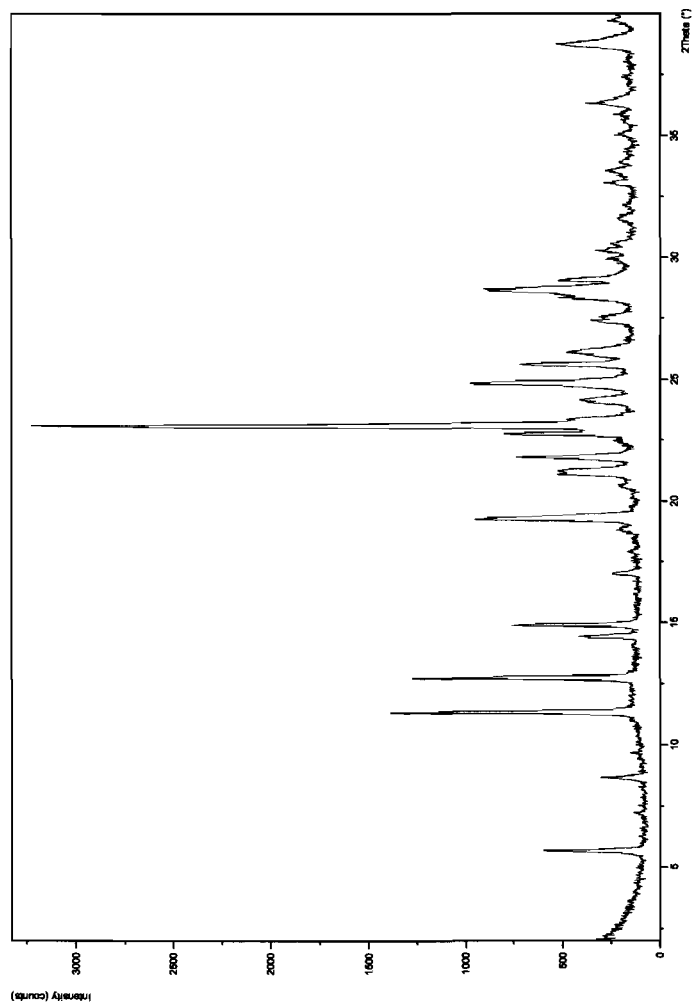
FIG. 1. Shows an XRPD diffractogram of Example 7A: trans-3-{[4-Fluoro-3-(trifluoromethyl)phenyl]oxy}-N-(imidazo[1,2-a]pyridin-8-ylmethyl)cyclobutanamine, hydrochloride salt FIG. 2. Shows an XRPD diffractogram of Example 7B: trans-3-{[4-Fluoro-3-(trifluoromethyl)phenyl]oxy}-N-(imidazo[1,2-a]pyridin-8-ylmethyl)cyclobutanamine, maleate salt.
Figure 2:
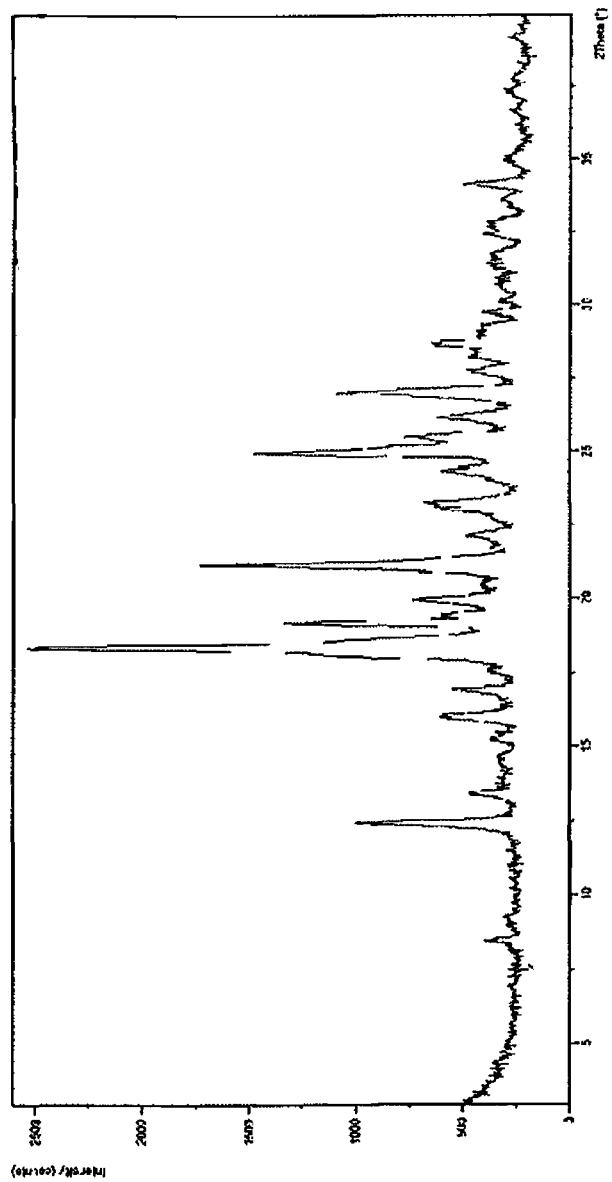
Figure 3:
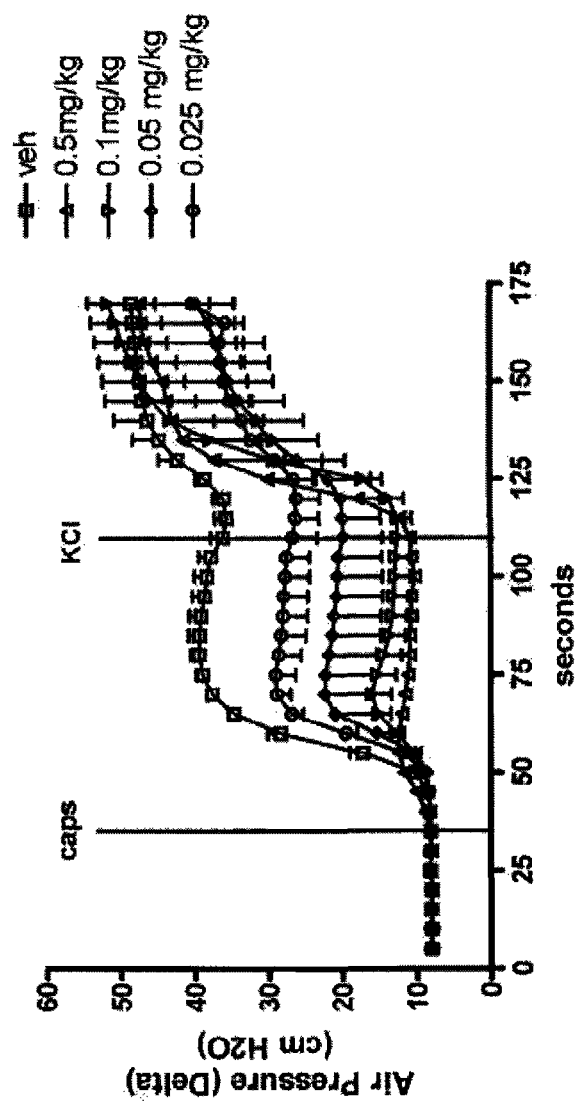
FIG. 3. Shows the Inhibition of i.v. Capsaicin induced bronchoconstriction in anesthetized Guinea pigs by intratracheal dosing of the compound of Example 7A.

What is claimed is:

1. A compound of formula (I)

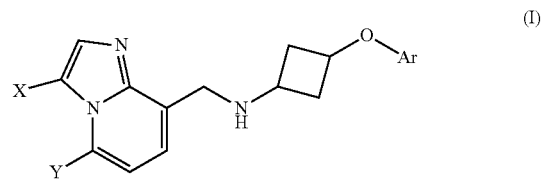

wherein

X represents a H atom, or a $CH_2OH$ group,

Y represents a H atom, or a $CH_2OH$ group, but X and Y are not both $CH_2OH$ groups and Ar is selected from

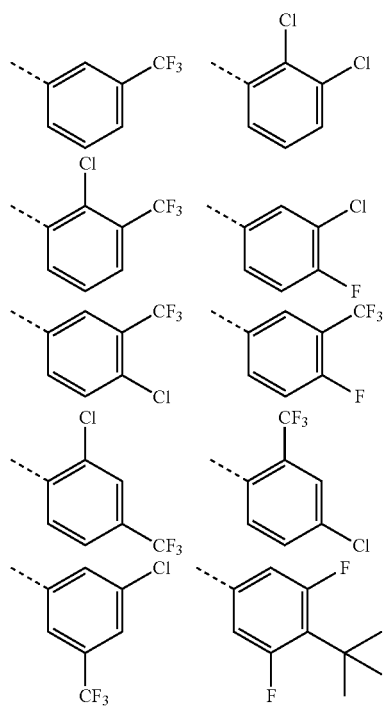

or a pharmaceutically acceptable salt thereof.

2. A compound according to claim 1 or a pharmaceutically acceptable salt thereof wherein X represents a hydrogen atom, and Y represents a $CH_2OH$ group.

3. A compound according to claim 1 or a pharmaceutically acceptable salt thereof wherein X represents a hydrogen atom and Y represents a hydrogen atom.

4. A compound according to claim 1 or a pharmaceutically acceptable salt thereof wherein X represents a $CH_2OH$ group and Y represents a hydrogen atom.

5. A compound according to claim 1 wherein the compound is selected from the group consisting of:
trans-N-(Imidazo[1,2-a]pyridin-8-ylmethyl)-3-{[3-(trifluoromethyl)phenyl]oxy}cyclobutanamine; trans-3-[(2,3-Dichlorophenyl)oxy]-N-(imidazo[1,2-a]pyridin-8-ylmethyl)cyclobutanamine;
cis-3-[(2,3-dichlorophenyl)oxy]-N-(imidazo[1,2-a]pyridin-8-ylmethyl)cyclobutanamine;
trans-3-{[2-Chloro-3-(trifluoromethyl)phenyl]oxy}-N-(imidazo[1,2-a]pyridin-8-ylmethyl)cyclobutanamine;
trans-3-[(3-Chloro-4-fluorophenyl)oxy]-N-(imidazo[1,2-a]pyridin-8-ylmethyl)cyclobutanamine trifluoroacetates;
trans-3-{[4-Chloro-3-(trifluoromethyl)phenyl]oxy}-N-(imidazo[1,2-a]pyridin-8-ylmethyl)cyclobutanamine;
trans-3-{[4-Fluoro-3-(trifluoromethyl)phenyl]oxy}-N-(imidazo[1,2-a]pyridin-8-ylmethyl)cyclobutanamine;
trans-3-{[2-Chloro-4-(trifluoromethyl)phenyl]oxy}-N-(imidazo[1,2-a]pyridin-8-ylmethyl)cyclobutanamine;
trans-3-{[4-Chloro-2-(trifluoromethyl)phenyl]oxy}-N-(imidazo[1,2-a]pyridin-8-ylmethyl)cyclobutanamine;
trans-3-{[3-Chloro-5-(trifluoromethyl)phenyl]oxy}-N-(imidazo[1,2-a]pyridin-8-ylmethyl)cyclobutanamine;
trans-3-{[4-(1,1-Dimethylethyl)-3,5-difluorophenyl]oxy}-N-(imidazo[1,2-a]pyridin-8-ylmethyl)cyclobutanamine;
cis-3-{[4-(1,1-Dimethylethyl)-3,5-difluorophenyl]oxy}-N-(imidazo[1,2-a]pyridin-8-ylmethyl)cyclobutanamine;
{8-[({trans-3-[(2,3-Dichlorophenyl)oxy]cyclobutyl}amino)methyl]imidazo[1,2-a]pyridin-5-yl}methanol;
(8-{[(trans-3-{[4-Fluoro-3-(trifluoromethyl)phenyl]oxy}cyclobutyl)amino]methyl}imidazo[1,2-a]pyridin-5-yl)methanol;
{8-[({trans-3-[(2,3-Dichlorophenyl)oxy]cyclobutyl}amino)methyl]imidazo[1,2-a]pyridin-3-yl}methanol;
cis-3-{[2-Chloro-3-(trifluoromethyl)phenyl]oxy}-N-(imidazo[1,2-a]pyridin-8-ylmethyl)cyclobutanamine; or
cis-3-{[4-Fluoro-3-(trifluoromethyl)phenyl]oxy}-N-(imidazo[1,2-a]pyridin-8-ylmethyl)cyclobutanamine; and pharmaceutically acceptable salts thereof.

6. A compound according to claim 5 wherein the compound is trans-3-{[4-Fluoro-3-(trifluoromethyl)phenyl]oxy}-N-(imidazo[1,2-a]pyridin-8-ylmethyl)cyclobutanamine; or a pharmaceutically acceptable salt thereof.

7. A pharmaceutical composition comprising a compound of formula (I) or a pharmaceutically acceptable salt thereof as defined in claim 1 and one or more pharmaceutically acceptable carriers or excipients.

8. A compound according to claim 1 wherein the compound is trans-3-{[4-Fluoro-3-(trifluoromethyl)phenyl]oxy}-N-(imidazo[1,2-a]pyridin-8-ylmethyl)cyclobutanamine or a pharmaceutically acceptable salt thereof.

* * * * *